US007247430B2

(12) United States Patent
Gicquel

(10) Patent No.: US 7,247,430 B2
(45) Date of Patent: Jul. 24, 2007

(54) **COMPOSITIONS AND METHODS FOR DETECTING MULTIDRUG RESISTANT STRAINS OF *M. TUBERCULOSIS* HAVING MUTATIONS IN GENES OF THE MUTT FAMILY**

(75) Inventor: Brigitte Gicquel, Paris (FR)

(73) Assignee: Institut Pasteur, Paris (FR)

( * ) Notice: Subject to any disclaimer, the term of this patent is extended or adjusted under 35 U.S.C. 154(b) by 467 days.

(21) Appl. No.: 10/216,817

(22) Filed: Aug. 13, 2002

(65) Prior Publication Data

US 2003/0129619 A1 Jul. 10, 2003

Related U.S. Application Data

(60) Provisional application No. 60/313,523, filed on Aug. 21, 2001, provisional application No. 60/311,824, filed on Aug. 14, 2001.

(51) Int. Cl.
*C12Q 1/68* (2006.01)
*C12P 19/34* (2006.01)
*C12N 1/20* (2006.01)
*C07H 21/04* (2006.01)

(52) U.S. Cl. ...................... 435/6; 435/91.2; 435/253.1; 536/23.1; 536/24.3

(58) Field of Classification Search ..................... None
See application file for complete search history.

(56) References Cited

FOREIGN PATENT DOCUMENTS

WO WO 00/36142 6/2000

OTHER PUBLICATIONS

Telenti, Mar. 1993, The Lancet, vol. 341, pp. 647 and 649.*
Van Rie, Feb. 2001, J. Clin. Micro., vol. 39, pp. 637 and 638.*
Rad, Jul. 2003, Emerg. Inf. Dis., vol. 9, p. 838.*
Glynn, Aug. 2002, Emerg. Inf. Dis., vol. 8, p. 843.*
Trautinger, Dec. 2002, EMBO J., vol. 21, p. 6944.*
Altschul et al., "Gapped BLAST and PSI-BLAST: A New Generation of Protein Database Search Programs," *Nucleic Acids Research*, vol. 25, pp. 3389-3402 (1997).
Bifani et al., "Identification of a W Variant Outbreak of *Mycobacterium tuberculosis* via Population-Based Molecular Epidemiology," *JAMA*, vol. 282, pp. 2321-2327 (1999).
Caminero et al., "Epidemiological Evidence of the Spread of a *Mycobacterium tuberculosis* Strain of the Beijing Geneotype on Gran Canaria Island," *American Journal of Respiratory and Critical Care Medicine*, vol. 164, pp. 1165-1170 (2001).
Cole et al., "Deciphering the Biology of *Mycobacterium tuberculosis* from the Complete Genome Sequence," *Nature*, vol. 393, pp. 537-544 (1998).
Cunningham, Richard P., "DNA Repair: Caretakers of the Genome?," *Current Biology*, pp. vol. 7, R576-R579 (1997).
Farmer et al., "Community Based Approaches to the Control of Multidrug Resistant Tuberculosis: Introducing "DOTS-plus"," *BMJ*, vol. 317, pp. 671-674 (1998).
Finken et al., "Molecular Basis of Streptomycin Resistance in *Mycobacterium tuberculosis*: Alterations of the Ribosomal Protein S12 Gene and Point Mutations Within a Functional 16S Ribosomal RNA Pseudoknot," *Molecular Microbiology*, vol. 9, pp. 1239-1246 (1993).
Giraud et al., "Costs and Benefits of High Mutation Rates: Adaptive Evolution of Bacteria in the Mouse Gut," *Science*, vol. 291, pp. 2606-2608 (2001).
Goguet et al., "Evaluation of Spoligotyping in a Study of the Transmission of *Mycrobacterium tuberculosis," Journal of Clinical Microbiology*, vol. 35, pp. 2210-2214 (1997).
Harris et al., "Mutational, Kinetic, and NMR Studies of the Roles of Conserved Glutamate Residues and of Lysine-39 in the Mechanism of the MutT Pyrophosphohydrolase," *Biochemistry*, vol 39, pp. 1655-1674 (2000).
Horst et al., "*Escherichia coli* Mutator Genes." *Trends in Microbiology*, vol. 7, pp. 29-36 (1999).
Kamerbeek et al., "Simultaneous Detection and Strain Differentiation of *Mycobacterium tuberculosis* for Diagnosis and Epidemiology," *Journal of Clinical Microbiology*, vol. 35, pp. 907-914 (1997).
Kremer et al., "Comparison of Methods Based on Different Molecular Epidemiological Markers for Typing of *Mycobacterium tuberculosis* Complex Strains: Interlaboratory Study of Discriminatory Power and Reproducibility," *Journal of Clinical Microbiology*, vol. 37, pp. 2607-2618 (1999).
Kubin et al., "A Multidrug-Resistant Tuberculosis Microepidemic Caused by Genetically Closely Relatec *Mycrobacterium tuberculosis* Strains," *Journal of Clinical Microbiology*, vol. 37, pp. 2715-2716 (1999).
Kurepina et al., "Characterization of the Phylogenetic Distribution and Chromosomal Insertion Sites of Five IS6110 Elements in *Mycobacterium tuberculosis*: Non-random Integration in the dnaA—dnaN Region," *Tubercle and Lung Disease*, vol. 79, pp. 31-42 (1998).
Mizrahi et al ., "DNA Repair in *Mycobacterium tuberculosis*. What Have we Learnt From the Genome Sequemce?," *Molecular Microbiology*, vol. 29, pp. 1331-1339 (1998).
Oliver et al., "High Frequency of Hypermutable *Pseudomonas aeruginosa* in Cystic Fibrosis Lung Infection," *Science*, vol. 288, pp. 1251-1253 (2000).
Pfyffer et al., "Multidrug-Resistant Tuberculosis in Prison Inmates, Azerbaijan," *Emerging Infections Disease*, vol. 7, pp. 855-861 (2001).
Rainey et al., "When Being Hyper Keeps you Fit," *Science*, vol. 288, pp. 1186-1187 (2000).

(Continued)

*Primary Examiner*—Ram R. Shukla
*Assistant Examiner*—Sarae Bausch
(74) *Attorney, Agent, or Firm*—Finnegan, Henderson, Farabow, Garrett & Dunner, L.L.P.

(57) ABSTRACT

The present invention pertains to polynucleotides derived from *M. tuberculosis* genes imparting resistance to antibiotics and chemically related compounds. This invention also relates to the use of the polynucleotides as oligonucleotide primers or probes for detecting *M. tuberculosis* strains that are resistant to antibiotics and related compounds in a biological sample. Kits containing the primers and probes are also provided.

14 Claims, 15 Drawing Sheets

OTHER PUBLICATIONS

Ritaco et al, "Nosocomial Spread of Human Immunodeficiency Virus-Related Multidrug-Resistant Tuberculosis in Buenos Aires," *The Journal of Infectious Diseases*, vol. 176, pp. 637-642 (1997).

Samper et al., "The Spanish Multidrug Resistant Tuberculosis Network," *Eurosurveillance*, vol. 5, pp. 43-45 (2000).

Sreevatsan et al., "Restricted Structural Gene Polymorphism in the *Mycrobacterium tuberculosis* Complex Indicates Evolutionarily Recent Global Dissemination," *Proc. Natl. Acad Sci. USA*, vol. 94, pp. 9869-9874 (1997).

Supply et al., "Automated High-Throughput Genotyping for Study of Global Epidemiology of *Mycobacterium tuberculosis* Based on Mycobacterial Interspersed Repetitive Units," *Journal of Clinical Microbiology*, vol. 39, pp. 3563-3571 (2001).

Taddei et al., "Counteraction by MutT Protein of Transcriptional Errors Caused by Oxidative Damage," *Science*, vol. 278, pp. 128-130 (1997).

Taddei et al., "Role of Mutator Alleles in Adaptive Evolution," *Nature*, vol. 387, pp. 700-702 (1997).

Telenti et al., "Detection of Rifampicin-Resistance Mutations in *Mycobacterium tuberculosis* " *The Lancet*, vol. 341, pp. 647-650 (1993).

Telzak et al., "Multidrug-Resistant Tuberculosis in Patients Without HIV Infection," *The New England Journal of Medicine*, vol. 333, pp. 907-911 (1995).

Tenaillon et al., "Mutators, Population Size, Adaptive Landscape and the Adaptation of Asexual Populations of Bacteria," *Genetics*, vol. 152, pp. 485-493 (1999).

Van Rie et al., Analysis for a Limited Number of Gene Codons Can Predict Drug Resistance of *Mycobacterium tuberculosis* in a High-Incidence Community, *Journal of Clinical Microbiology*, vol. 39, pp. 636-641 (2001).

Van Soolingen et al., "Predominance of a Single Genotype of *Mycobacterium tuberculosis* in Countries of East Asia," *Journal of Clinical Microbiology*, vol. 33, pp. 3234-3238 (1995).

U.S. Appl. No. 10/777,131, (WO 03/016562 A2).

Karunakaran, Ponniah et al., "Genetic Antagonism and Hypermutability in *Mycobacterium smegmatis,*" *Journal of Bacteriology*, pp. 3331-3335 (2000).

Kremer, Kristin et al., "Selective Advantages of the Beijing Genotype of *M. tuberculosis* in Several Georgrahic Regions," *Abstracts Oral Presentations*, p. 25 (2000).

Rigouts, L. et al., "Beijing Genotype Present Among Drug-Resistant *Mycobacterium tuberculosis* Isolates from Central and Western Asia," *Abstracts Oral Presentations*, p. 26 (2000).

Office Action mailed Nov. 15, 2005, U.S. Appl. No. 10/777,131 (7 pages +4 pgs. init. PTO-1449+1 pg. PTO-892).

* cited by examiner

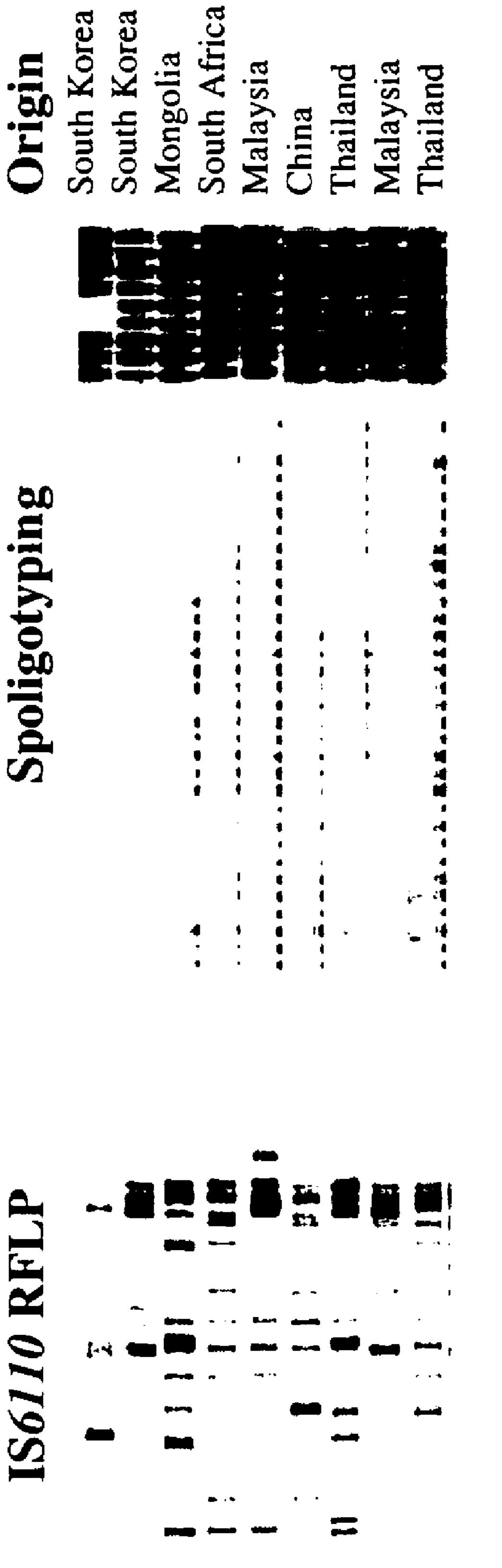
Figure 1: Characteristic patterns of *M. tuberculosis* Beijing genotype strains

FIGURE 2A

SEQ ID NO: 17

Location (from Cole et al.; Nature)

alkA: M. tuberculosis

```
             ttggtcaacaagttcgagggggacgcgtcgct
aaccatcttcggcgccccgaaccggcttccctgtcccga
agacaaggcactggccgccgcgcgggcgatagccgatcg
gctggtcaacgaaatgcccgagtgccaggccgggatcgg
cgtggcggcggggcaggtcattgccggcaacgtgggtgc
ccgagaacggttcgagtacaccgtgatcggggagccggt
caacgaggcggcccgattgtgcgaactggccaaatcgcg
tcccggcaagttgctggcttcggcacaggccgtggacgc
cgcaagcgaagaggagcgcgcccgttggtctttgggtag
gcatgtgaaacttcgtgggcacgaccaaccggtccggct
ggccaagccggtcgggctgaccaagccgcgtaggtaacc    F (SEQ ID NO: 5)
tgcccgaacccacgacgaccccatcacaatgtcgttttt
ccgccagtcatgtcggtgggcgggtgtaattgttgaagg
   1 - gtg cac gac gac ttc gaa cgc tgc tac cgg
  31 - gcg atc cag tcc aaa gac gcc cgg ttc gac
  61 - ggc tgg ttc gtc gtc gcg gtt ttg acc acc
  91 - ggt gtc tac tgc cgg ccg agt tgc ccc gtc
 121 - cgg cca ccg ttc gcg cgc aat gtc cgg ttc
 151 - ctg ccg act gcg gcg gcc gct cag ggg gag
 181 - gga ttc cgg gcc tgc aaa cgg tgc cgc ccc
 211 - gac gcc tcg cct ggg tct ccg gaa tgg aat
 241 - gtg cgt agt gac gtc gtg gcg cgg gcg atg
 271 - cgg ctg att gcc gac gga acg gtg gac cgc
 301 - gac ggt gtc agc ggc ctc gcg gcc cag ctc
 331 - ggt tac acc att cgc cag ctg gag cgg ctg
 361 - ttg cag gcc gtg gtc ggc gcc ggt ccg ctc
 391 - gcg ttg gcc cgc gcc caa cgc atg cag acc
 421 - gcc cgg gtg ctg atc gag acc acg aac ctg
 451 - ccg ttc ggc gat gtc gca ttc gcc gcc ggg
 481 - ttt tcc agc atc cgt cag ttc aac gac acc
 511 - gtt cgc ctg gcg tgc gac ggc aca ccg acg
 541 - gca ttg cgt gcg cgc gcg gcc gcc cga ttc
 571 - gag tct gcc acc gca tca gcg ggc acg gtg
 601 - tcg ctg cgg cta ccc gtc cgt gca cca ttc
 631 - gcc ttc gag ggt gtt ttc ggc cat ctg gcc
 661 - gcc acc gcg gtg ccg ggt tgc gaa gag gtc
 691 - cgc gat ggt gcg tac cga cgc acg cta cgg
 721 - ctc cca tgg ggc aac ggc atc gtc agc ctg
 751 - acg ccg gca ccc gat cat gtg cgc tgc ctg
 781 - ctt gtg ctc gat gat ttc cgc gac ctg atg
 811 - acg gcc act gca cgt tgc cga cgg ctg ctg
 841 - gac ctc gac gcc gat ccc gaa gcg atc gtc
 871 - gag gcg ctg ggc gcc gat ccg gat ctg cgc
 901 - gca gtg gtg ggc aag gca ccc ggg caa cgc
 931 - att ccc cgc aca gtc gac gag gca gaa ttc
 961 - gcc gtg cgg gcg gtc ctc gcc caa cag gta
 991 - tcg acg aag gcc gca agc act cac gcg ggc
1021 - cga ctg gtc gcc gcc tac gga cgg ccg gtc
1051 - cac gat cgc cac ggc gct ttg acc cac acc
1081 - ttc ccg tcg atc gag cag ctc gct gag atc
1111 - gat ccc ggc cat ctg gcc gtc ccc aag gcg
1141 - cgt caa agg acc ata aac gcg ctc gtc gcc
1171 - agc ctt gcc gac aaa agt ctg gtc ctg gac
1201 - gcc gga tgt gac tgg caa cgc gcc cgc ggg
1231 - cag ttg cta gcg ctg ccc gga gtg ggc ccc
1261 - tgg acc gcg gag gtc atc gcc atg cgc ggc
1291 - ctc ggt gac ccg gac gcc ttt ccg gcc agt
```

FIGURE 2B

```
1321 - gat ctc ggc ctg cgg ctg gcc gcc aaa aag
1351 - ctg ggc ctg cct gca caa cga cga gcc ctg
1381 - acg gtg cac agc gct cgc tgg cgc ccc tgg
1411 - cgc tcc tat gcc acc cag cac ctg tgg acc
1441 - acc ctg gaa cat ccg gta aac caa tgg cca
1471 - ccg cag gag aag atc gca
       tgattcactaccgcaccatcgatagccccatcgggccat
       taaccctggccgggcatggctcggtgttgacgaacctgc
       ggatgctcgagcagacgtatgagccaagccgcacacact
       ggacacccgaccccggcgcattttctggcgctgtcgacc
       aactcaacgcttatttcgccggcgagctcaccgaattcg
       atgtggaacttgacctccggggaaccgactttcagcaac
       gagtatggaaagcattgctgacaatcccgtacggggaaa
       cccggtcctacggggaaatcgccgaccagatcggcgccc
       ccggcgccgcacgcgccgtgggattggccaacggccaca
       atcccatcgccatcatcgtcccgtgccaccgcgtgatcg
       gcgccagcggaaagctcaccgggtacggcggtggaatca
       accggaaacgagctctgctcgagttggagaaaagccggg
       cgcccgcagacttgacgctcttcgactgagcg
```

R (SEQ ID NO: 6)

FIGURE 2C

>alkA ORF: 1488 bp - M. tuberculosis -

SEQ ID NO: 27 gtgcacgacgacttcgaacgctgctaccgggcgatccagtccaaagacgcccggttcgac
ggctggttcgtcgtcgcggttttgaccaccggtgtctactgccggccgagttgccccgtc
cggccaccgttcgcgcgcaatgtccggttcctgccgactgcggcggccgctcaggggag
ggattccgggcctgcaaacggtgccgccccgacgcctcgcctgggtctccggaatggaat
gtgcgtagtgacgtcgtggcgcgggcgatgcggctgattgccgacggaacggtggaccgc
gacggtgtcagcggcctcgcggcccagctcggttacaccattcgccagctggagcggctg
ttgcaggccgtggtcggcgccggtccgctcgcgttggcccgcgcccaacgcatgcagacc
gcccgggtgctgatcgagaccacgaacctgccgttcggcgatgtcgcattcgccgccggg
ttttccagcatccgtcagttcaacgacaccgttcgcctggcgtgcgacggcacaccgacg
gcattgcgtgcgcgcgcggccgcccgattcgagtctgccaccgcatcagcgggcacggtg
tcgctgcggctacccgtccgtgcaccattcgccttcgagggtgttttcggccatctggcc
gccaccgcggtgccgggttgcgaagaggtccgcgatggtgcgtaccgacgcacgctacgg
ctcccatggggcaacggcatcgtcagcctgacgccggcacccgatcatgtgcgctgcctg
cttgtgctcgatgatttccgcgacctgatgacggccactgcacgttgccgacggctgctg
gacctcgacgccgatcccgaagcgatcgtcgaggcgctgggcgccgatccggatctgcgc
gcagtggtgggcaaggcacccgggcaacgcattccccgcacagtcgacgaggcagaattc
gccgtgcgggcggtcctcgcccaacaggtatcgacgaaggccgcaagcactcacgcgggc
cgactggtcgccgcctacggacggccggtccacgatcgccacggcgctttgacccacacc
ttcccgtcgatcgagcagctcgctgagatcgatcccggccatctggccgtccccaaggcg
cgtcaaaggaccataaacgcgctcgtcgccgccggatgtgactggcaacgcgcccgcggg
cagttgctagcgctgcccggagtgggcccctggaccgcggaggtcatcgccatgcgcggc
ctcggtgacccggacgcctttccggccagtgatctcggcctgcggctggccgccaaaaag
ctgggcctgcctgcacaacgacgagccctgacggtgcacagcgctcgctggcgcccctgg
cgctcctatgccacccagcacctgtggaccaccctggaacatccggtaaaccaatggcca
ccgcaggagaagatcgca FIGURE 3A ogt: M. tuberculosis

```
                                                ggcct
       cggtgacccggacgcctttccggccagtgatctcggcct
       gcggctggccgccaaaaagctgggcctgcctgcacaacg
       acgagccctgacggtgcacagcgctcgctggcgcccctg     F  (SEQ ID NO: 7)
       gcgctcctatgccacccagcacctgtggaccaccctgga
       acatccggtaaaccaatggccaccgcaggagaagatcgc     SEQ ID NO: 18
   1 - atg att cac tac cgc acc atc gat agc ccc
  31 - atc ggg cca tta acc ctg gcc ggg cat ggc
  61 - tcg gtg ttg acg aac ctg cgg atg ctc gag
  91 - cag acg tat gag cca agc cgc aca cac tgg     Location 1=1.477.137
 121 - aca ccc gac ccc ggc gca ttt tct ggc gct
 151 - gtc gac caa ctc aac gct tat ttc gcc ggc
 181 - gag ctc acc gaa ttc gat gtg gaa ctt gac
 211 - ctc cgg gga acc gac ttt cag caa cga gta
 241 - tgg aaa gca ttg ctg aca atc ccg tac ggg
 271 - gaa acc cgg tcc tac ggg gaa atc gcc gac
 301 - cag atc ggc gcc ccc ggc gcc gca cgc gcc
 331 - gtg gga ttg gcc aac ggc cac aat ccc atc
 361 - gcc atc atc gtc ccg tgc cac cgc gtg atc
 391 - ggc gcc agc gga aag ctc acc ggg tac ggc
 421 - ggt gga atc aac cgg aaa cga gct ctg ctc
 451 - gag ttg gag aaa agc cgg gcg ccc gca gac
 481 - ttg acg ctc ttc gac
       tgagcgcccccgcccgcgagggtatcgtcattgcgaaaa
       tcgaagccataattcgcccgctcgcgagcggctgagtcg     R (SEQ ID NO: 8)
       atataaacatacaaaaacaccaccgttaccgggggtgtt
       tttgtatgttcggcggtgtcctacttttccacccggagg
       ggcagtatcatcggcgctggcaggcttagcttccgggtt
       cggaa
```

FIGURE 3B

>ogt ORF: 495 bp - M. tuberculosis -
atgattcactaccgcaccatcgatagccccatcgggccattaaccctggccgggcatggc
tcggtgttgacgaacctgcggatgctcgagcagacgtatgagccaagccgcacacactgg
acacccgaccccggcgcattttctggcgctgtcgaccaactcaacgcttatttcgccggc
gagctcaccgaattcgatgtggaacttgacctccggggaaccgactttcagcaacgagta
tggaaagcattgctgacaatcccgtacggggaaacccggtcctacggggaaatcgccgac
cagatcggcgcccccggcgccgcacgcgccgtgggattggccaacggccacaatcccatc
gccatcatcgtcccgtgccaccgcgtgatcggcgccagcggaaagctcaccgggtacggc
ggtggaatcaaccggaaacgagctctgctcgagttggagaaaagccgggcgcccgcagac
ttgacgctcttcgac

SEQ ID NO: 28

FIGURE 4A mutT2: M. tuberculosis

```
                                        gatgt      F (SEQ ID NO: 1)
        ccggatgatgatttacctcctcggctcgctcggccaccc
        ggcgtacggcgtcgataccggccataaacgtcggaaact
        tgattgacctacgcaggacaccaccggcgcgctgccagc
        cgttgaggtcgtgcagtgcggcgtcgacctgctcatccg
        ttaacacagccatacctcgacggtataccgtcacaggtc
  1 - atg ctg aat cag atc gtg gtt gcc gga gcc
 31 - atc gtc cgc ggt tgc acg gtc ttg gtg gcg
 61 - caa cgc gtt cgg cca ccg gag ttg gcg ggt
 91 - cgt tgg gaa ctt ccc ggc ggt aag gtc gcc
121 - gcc ggc gaa acc gag cgc gcc gcg ctg gcc
151 - cga gag ctc gcc gaa gaa ctg gga ctc gag
181 - gtc gcc gac ctc gcg gtg ggc gac cgt gtg
211 - ggc gac gat att gcg ttg aac ggc acg acg
241 - acg ctg cgg gcc tat cgc gtg cat ctg ctt
271 - ggc ggc gaa ccg cgt gcg cgt gac cac cgg
301 - gcg ctg tgc tgg gtg acg gcg gcc gaa ctg
331 - cac gat gtc gac tgg gta cca gcc gac cgc
361 - ggc tgg att gcg gac ctg gcg cga acc ctc
391 - aac ggg tcc gcc gca gat gtc cac cgt cgc
421 - tgt
        taggaaaccgacggtgtggttgacggtggccgccgtcaa
        cttggttagaacaacgtgacaaaacgttaacttgggttt
        gcatgcccgtagcgattacgatggttttctggacgcgtg
        gcgacaacttccgggcaggacgctgacgcccatccatcg
        agatacccgatgttgacgagaggggtccccgacccggcg    R (SEQ ID NO: 2)
        gaccg
```

SEQ ID NO: 19

Location 1=1.286.595

FIGURE 4B

```
>mutT2 ORF: 423 bp - M. tuberculosis -
atgctgaatcagatcgtggttgccggagccatcgtccgcggttgcacggtcttggtggcg
caacgcgttcggccaccggagttggcgggtcgttgggaacttcccggcggtaaggtcgcc
gccggcgaaaccgagcgcgccgcgctggcccgagagctcgccgaagaactgggactcgag
gtcgccgacctcgcggtgggcgaccgtgtgggcgacgatattgcgttgaacggcacgacg
acgctgcgggcctatcgcgtgcatctgcttggcggcgaaccgcgtgcgcgtgaccaccgg
gcgctgtgctgggtgacggcggccgaactgcacgatgtcgactgggtaccagccgaccgc
ggctggattgcggacctggcgcgaaccctcaacgggtccgccgcagatgtccaccgtcgc
tgt
```

SEQ ID NO: 29

FIGURE 5A

Rv3908: M. tuberculosis

SEQ ID NO: 20

Location 1=4.393.449

```
                                            tgtcg
        ctcgaaggtgggcaaatcgtgcgcccccgacacagcgac       F (SEQ ID NO: 3)
        ttctgtgatagatgtgactggcgcgactcaattggtcag
        cgcgggtcgcctgcaccgccccgctccctcgcccaacga
        ataagtcctggccgacgatgggcgctcagacggcgagta
        catcgggaacacccgcccgtaccagctactatcgctggg
  1 - gtg tcc gac ggc gaa caa gcc aaa tca cgt
 31 - cga cgc cgg ggg cgg cgc cgc ggg cgg cgc
 61 - gct gcg gct aca gcc gag aat cac atg gac
 91 - gcc caa ccg gcc ggc gac gcc acc ccg acc
121 - ccg gca acg gcg aag cgg tcc cgg tcc cgc
151 - tca cct cgt cgc ggg tcg act cgg atg cgc
181 - acc gtg cac gaa aca tcg gct gga ggg ttg
211 - gtc att gac ggt atc gac ggt cca cga gac
241 - gcg cag gtc gcg gct ctg atc ggc cgc gtc
271 - gac cgg cgc ggc cgg ctg ctg tgg tcg cta
301 - ccc aag ggg cac atc gag ttg ggc gag acc
331 - gcc gag cag acc gcc atc cgc gag gtc gcc
361 - gag gag acc ggc atc cgc ggc agt gtg ctc
391 - gcc gcg ctg ggg cgc atc gac tac tgg ttc
421 - gtc acc gac ggc cgg cgg gtg cac aag acc
451 - gtc cac cat tat ttg atg cgg ttt tta ggc
481 - gga gag ctg tcc gac gaa gac ctc gag gta
511 - gcc gag gta gcc tgg gtg ccg atc cgg gaa
541 - ctg ccg tct cga ctg gcc tac gcc gac gaa
571 - cgt cga cta gcc gag gtg gcc gac gaa ctg
601 - atc gac aag ctg cag agc gac ggc ccc gcc
631 - gcg ctt ccg ccg cta cca ccc agc tcg cct
661 - cgt cga cgg ccg caa acg cat tca cgc gct
691 - cgt cat gcc gat gac tca gca ccg ggt cag
721 - cac aac ggt ccc ggg ccg ggg ccg
        tgaccgcactgcaactcggctgggccgctttggcgcgcg
        tcacctcagcgatcggcgtcgtggccggcctcgggatgg
        cgctcacggtaccgtcggcggcaccgcacgcgctcgcag
        gcgagcccagcccgacgccttttgtccaggtccgcatcg
        atcaggtgaccccggacgtggtgaccacttccagcgaac       R (SEQ ID NO: 4)
        cccat
```

FIGURE 5B

>Rv3908 ORF: 744 bp - M. tuberculosis -
gtgtccgacggcgaacaagccaaatcacgtcgacgccgggggcggcgccgcgggcggcgc
gctgcggctacagccgagaatcacatggacgcccaaccggccggcgacgccaccccgacc
ccggcaacggcgaagcggtcccggtcccgctcacctcgtcgcgggtcgactcggatgcgc
accgtgcacgaaacatcggctggagggttggtcattgacggtatcgacggtccacgagac
gcgcaggtcgcggctctgatcggccgcgtcgaccggcgcggccggctgctgtggtcgcta
cccaaggggcacatcgagttgggcgagaccgccgagcagaccgccatccgcgaggtcgcc
gaggagaccggcatccgcggcagtgtgctcgccgcgctggggcgcatcgactactggttc
gtcaccgacggccggcgggtgcacaagaccgtccaccattatttgatgcggtttttaggc
ggagagctgtccgacgaagacctcgaggtagccgaggtagcctgggtgccgatccgggaa
ctgccgtctcgactggcctacgccgacgaacgtcgactagccgaggtggccgacgaactg
atcgacaagctgcagagcgacggccccgccgcgcttccgccgctaccacccagctcgcct
cgtcgacggccgcaaacgcattcacgcgctcgtcatgccgatgactcagcaccgggtcag
cacaacggtcccgggccggggccg

SEQ ID NO: 30

FIGURE 6A mutY: M. tuberculosis

```
                                             cgccc
      aggccttggtcgaagatgatctcagcggccactcggctg
      tccgcgcagccgaagatcaccgccgtgggcttctgcccg
      gcggccaagccggctcggtggtcgacgctctgactggga
      tgctggggccggccggcgacgaatcgctcgttaccctct      F (SEQ ID NO: 9)
      ttgagtgctttccacgcggctaccggattggtgttgggc
  1 - atg cct cac ata ctg ccg gaa ccg tcg gtg
 31 - acc ggc ccg cga cac ata tca gat acc aat
 61 - ctt ctc gct tgg tat cag cga tcg cac cgg
 91 - gat ctg ccc tgg cga gag ccc ggt gtc agc
121 - ccg tgg cag atc ctg gtc agc gag ttc atg
151 - ctg cag cag acg ccg gcc gcc cgg gtg ctg
181 - gcg atc tgg ccg gac tgg gtg cgg cgg tgg
211 - ccc acg ccg tcg gcc acc gcc acg gcc agc
241 - acc gcc gat gtg tta cgc gcc tgg ggc aag
271 - ctg ggc tat ccc agg cga gcc aag cgc tta
301 - cac gag tgc gcc acc gtc atc gcc cgc gac
331 - cac aat gac gtg gtg ccc gac gat atc gag
361 - atc ctg gtc acc ctg ccg ggc gtc ggg agc
391 - tac acc gcg cgc gcg gtg gcg tgt ttc gct
421 - tac cgc cag cgg gtg ccg gtg gtg gac acc
451 - aat gtg cgg cgc gtg gtg gcc cgc gcc gtt
481 - cac ggc cgc gcc gac gcc ggt gcg cca tcg
511 - gtg ccg cgc gac cac gcc gac gtc ttg gcg
541 - ctg ttg ccg cac cgc gag acg gcg cct gaa
571 - ttt tcg gtc gcg ctg atg gag ttg ggt gcg
601 - acg gtg tgc acc gcc cgc aca ccc cgg tgc
631 - ggg tta tgc ccg ctg gac tgg tgc gca tgg
661 - cgg cat gcc ggt tat ccg ccg tcg gac ggt
691 - ccg ccg cgc cgg ggg cag gcc tac acc gga
721 - acc gac cgc caa gtc cgc gga cgg tta ctg
751 - gat gtg ttg cgc gcc gcg gag ttt ccc gtc
781 - acc cgg gcc gag ttg gac gtg gcg tgg ctg
811 - acc gat acc gca cag cgt gac cgg gcg ctg
841 - gag tcg ctg ctg gcc gat gcg ctg gtg acc
871 - cgg acg gtc gat ggc cgg ttc gcg ttg ccc
901 - ggc gaa ggg ttt
      tagccgggtaggccgtccgcaccggcggcgccgaaaccg
      ccgggatcaccggggttgcccgcgacgactgtcccagct      R (SEQ ID NO: 10)
      cccgcggcgccacccgcgccgccagcgccgccggcacct
      ccctggcccccggtaccgcccgcaccgtggacacctggc
      tggctgaacattccggcacctccgccggcacctccggca
      ccgcc
```

SEQ ID NO: 21

Location 1=4.030.493

FIGURE 6B

SEQ ID NO: 31

```
>mutY ORF: 912 bp - M. tuberculosis -
atgcctcacatactgccggaaccgtcggtgaccggcccgcgacacatatcagataccaat
cttctcgcttggtatcagcgatcgcaccgggatctgccctggcgagagcccggtgtcagc
ccgtggcagatcctggtcagcgagttcatgctgcagcagacgccggccgcccgggtgctg
gcgatctggccggactgggtgcggcggtggcccacgccgtcggccaccgccacggccagc
accgccgatgtgttacgcgcctggggcaagctgggctatcccaggcgagccaagcgctta
cacgagtgcgccaccgtcatcgcccgcgaccacaatgacgtggtgcccgacgatatcgag
atcctggtcaccctgccgggcgtcgggagctacaccgcgcgcgcggtggcgtgtttcgct
taccgccagcgggtgccggtggtggacaccaatgtgcggcgcgtggtggcccgcgccgtt
cacggccgcgccgacgccggtgcgccatcggtgccgcgcgaccacgccgacgtcttggcg
ctgttgccgcaccgcgagacggcgcctgaattttcggtcgcgctgatggagttgggtgcg
acggtgtgcaccgcccgcacaccccggtgcgggttatgcccgctggactggtgcgcatgg
cggcatgccggttatccgccgtcggacggtccgccgcgccgggggcaggcctacaccgga
accgaccgccaagtccgcggacggttactggatgtgttgcgcgccgcggagtttcccgtc
acccgggccgagttggacgtggcgtggctgaccgataccgcacagcgtgaccgggcgctg
gagtcgctgctggccgatgcgctggtgacccggacggtcgatggccggttcgcgttgccc
ggcgaagggttt
```

FIGURE 7A

Rv3909: M. tuberculosis

```
                                       ccgtc
      tcgactggcctacgccgacgaacgtcgactagccgaggt
      ggccgacgaactgatcgacaagctgcagagcgacggccc
      cgccgcgcttccgccgctaccacccagctcgcctcgtcg
      acggccgcaaacgcattcacgcgctcgtcatgccgatga
      ctcagcaccgggtcagcacaacggtcccgggccggggcc
   1 - gtg acc gca ctg caa ctc ggc tgg gcc gct
  31 - ttg gcg cgc gtc acc tca gcg atc ggc gtc
  61 - gtg gcc ggc ctc ggg atg gcg ctc acg gta
  91 - ccg tcg gcg gca ccg cac gcg ctc gca ggc
 121 - gag ccc agc ccg acg cct ttt gtc cag gtc
 151 - cgc atc gat cag gtg acc ccg gac gtg gtg
 181 - acc act tcc agc gaa ccc cat gtc acc gtc
 211 - agc gga acg gtg acc aat acc ggt gac cgc
 241 - cca gtc cgc gat gtg atg gtc cgg ctt gag
 271 - cac gcc gcc gcg gtc acg tcg tca acg gcg
 301 - tta cgc acc tcg ctc gac ggc ggc acc gac
 331 - cag tac cag ccg gcc gcg gac ttc ctc acg
 361 - gtc gcc ccc gaa cta gac cgc ggg caa gag
 391 - gcc ggc ttt acc ctc tcg gcc ccg ctg cgc
 421 - tcg ctg acc agg ccg tcg ttg gcc gtc aac
 451 - cag ccc ggg atc tac ccg gtc ctg gtc aac
 481 - gtc aat ggg aca ccc gac tac ggt gcg cct
 511 - gcg cgg ctc gac aat gcg cgg ttc ctg ttg
 541 - ccc gtg gtc gga gtg cca ccc gac cag gcc
 571 - acc gac ttc ggc tcc gct gtt gca cca gaa
 601 - acg acg gcg ccg gtc tgg atc acc atg ctg
 631 - tgg ccg ctg gcc gac cgg ccc cgg ttg gcc
 661 - ccc ggg gca ccc ggt ggc acc gtt ccc gtc
 691 - cgg ctg gtc gac gac gac ctg gca aac tcg
 721 - ctg gcc aac ggc ggc cgg ctg gac atc ctc
 751 - ctg tcg gcg gcc gag ttc gcc acc aac cgg
 781 - gaa gtc gac ccc gac ggc gcc gtc ggc cga
 811 - gcg ctg tgc ctg gcc atc gac cca gat cta
 841 - ctc atc acc gtc aat gcg atg acc ggc ggc
 871 - tac gtc gtg tcc gac tcg ccc gac ggg gcc
 901 - gct caa cta ccg ggc acc ccg acc cac ccg
 931 - ggc acc ggc cag gcc gcc gca tcc agc tgg
 961 - ctg gat cga ttg cgg acg cta gtc cac cgg
 991 - aca tgc gtg acg ccg ctg cct ttt gcc caa
1021 - gcc gac ctg gat gct ttg cag cgg gtt aat
1051 - gat ccg agg ctg agc gcg atc gca acc atc
1081 - agc ccc gcc gac atc gtc gac cgc atc ctg
1111 - gat gtc agc tcc acc cgc ggc gca acc gtg
1141 - ctg ccc gac ggc ccg ttg acc ggc cgg gcg
1171 - atc aac ttg ctc agc acc cac ggc aac acg
1201 - gtt gcc gtc gcg gcc gcc gat ttt agc ccc
1231 - gag gaa cag cag ggt tcg tcc cag atc ggc
1261 - tcc gcg ctc tta ccc gct acc gcg ccc cgg
1291 - cgg ttg tcc ccg cgg gtg gta gcg gcg ccg
1321 - ttt gat ccc gcg gtc ggg gcc gcg ctg gcc
1351 - gcc gcg gga aca aac ccg acc gtt cct acc
1381 - tat cta gat ccc tcg ttg ttc gtt cgg atc
1411 - gcg cat gaa tcg atc acc gcg cgc cgc cag
1441 - gac gcc ttg ggc gca atg ctg tgg cgc agc
1471 - ttg gag ccg aat gcc gcg ccc cgt acc caa
1501 - atc ctg gtg ccg ccg gcg tcg tgg agc ctg
```

SEQ ID NO: 22

Location 1=4.394.192

Direction (+)

FIGURE 7B

1531 - gcc agc gac gac gcg cag gtc atc ctg acc
1561 - gcg ctg gcc acc gcc atc cgg tct ggc ctg
1591 - gcc gtg ccg cga cca cta ccg gcg gtg atc
1621 - gct gac gcc gcg gcc cgc acc gag cca ccg
1651 - gaa ccc ccg ggc gct tac agc gcc gct cgc
1681 - ggc cgg ttc aat gac gac atc acc acg cag
1711 - atc ggc ggg cag gtt gcc cgg cta tgg aag
1741 - ctg acc tcg gcg ttg acc atc gat gac cgc
1771 - acc ggg ctg acc ggc gtg cag tac acc gca
1801 - cca cta cgc gag gac atg ttg cgc gcg ctg
1831 - agc caa tcg cta cca ccc gat acc cgc aac
1861 - ggg ctg gcc cag cag cgg ctg gcc gtc gtt
1891 - gga aag acg atc gac gat ctt ttc ggc gcg
1921 - gtg acc atc gtc aac ccg ggc ggc tcc tac
1951 - act ctg gcc acc gag cac agt ccg ctg ccg
1981 - ttg gcg ctg cat aat ggc ctc gcc gtg cca
2011 - atc cgg gtc cgg cta cag gtc gat gct ccg
2041 - ccc ggg atg acg gtg gcc gat gtc ggt cag
2071 - atc gag cta ccg ccc ggg tac ctg ccg cta
2101 - cga gta cca atc gag gtg aac ttc aca cag
2131 - cgg gtt gcc gtc gac gtg tcg ctg cgg acc
2161 - ccc gac ggc gtc gcg ctg ggt gaa ccg gtg
2191 - cgg ttg tcg gtg cac tcc aac gcc tac ggc
2221 - aag gtg ttg ttc gcg atc acg cta tcc gct
2251 - gcg gcc gtg ctg gta acg ctg gcg ggc cgg
2281 - cgc ctt tgg cac cgg ttc cgt ggc cag cct
2311 - gat cgc gcc gac ctg gat cgc ccc gac ctg
2341 - cct acc ggc aaa cac gcc ccg cag cgc cgt
2371 - gcc gta gcc agt cgg gat gac gaa aag cac
2401 - cgg gta
tgagaccctcccctggagaggtgcccacggcatcgcaga
ggcagcccgagctgtccgacgcggcgctggtatcgcact
cctgggcaatggcattcgcgacgctgatcagccggatca
ccggctttgcccggatcgtgctgctggccgcgatcttag
gtgcggcgctggccagctcgttctcggtggccaaccagc
tgccg

FIGURE 7C

SEQ ID NO: 32

>Rv3909 ORF: 2406 bp - M. tuberculosis -
gtgaccgcactgcaactcggctgggccgctttggcgcgcgtcacctcagcgatcggcgtc
gtggccggcctcgggatggcgctcacggtaccgtcggcggcaccgcacgcgctcgcaggc
gagcccagcccgacgccttttgtccaggtccgcatcgatcaggtgaccccggacgtggtg
accacttccagcgaaccccatgtcaccgtcagcggaacggtgaccaataccggtgaccgc
ccagtccgcgatgtgatggtccggcttgagcacgccgccgcggtcacgtcgtcaacggcg
ttacgcacctcgctcgacggcggcaccgaccagtaccagccggccgcggacttcctcacg
gtcgcccccgaactagaccgcgggcaagaggccggctttaccctctcggccccgctgcgc
tcgctgaccaggccgtcgttggccgtcaaccagcccgggatctacccggtcctggtcaac
gtcaatgggacacccgactacggtgcgcctgcgcggctcgacaatgcgcggttcctgttg
cccgtggtcggagtgccacccgaccaggccaccgacttcggctccgctgttgcaccagaa
acgacggcgccggtctggatcaccatgctgtggccgctggccgaccggccccggttggcc
cccggggcacccggtggcaccgttcccgtccggctggtcgacgacgacctggcaaactcg
ctggccaacggcggccggctggacatcctcctgtcggcggccgagttcgccaccaaccgg
gaagtcgaccccgacggcgccgtcggccgagcgctgtgcctggccatcgacccagatcta
ctcatcaccgtcaatgcgatgaccggcggctacgtcgtgtccgactcgcccgacggggcc
gctcaactaccgggcaccccgacccacccgggcaccggccaggccgccgcatccagctgg
ctggatcgattgcggacgctagtccaccggacatgcgtgacgccgctgccttttgcccaa
gccgacctggatgctttgcagcgggttaatgatccgaggctgagcgcgatcgcaaccatc
agccccgccgacatcgtcgaccgcatcctggatgtcagctccacccgcggcgcaaccgtg
ctgcccgacggcccgttgaccggccgggcgatcaacttgctcagcacccacggcaacacg
gttgccgtcgcggccgccgattttagccccgaggaacagcagggttcgtcccagatcggc
tccgcgctcttacccgctaccgcgccccggcggttgtccccgcgggtggtagcggcgccg
tttgatcccgcggtcggggccgcgctggccgccgcgggaacaaacccgaccgttcctacc
tatctagatccctcgttgttcgttcggatcgcgcatgaatcgatcaccgcgcgccgccag
gacgccttgggcgcaatgctgtggcgcagcttggagccgaatgccgcgccccgtacccaa
atcctggtgccgccggcgtcgtggagcctggccagcgacgacgcgcaggtcatcctgacc
gcgctggccaccgccatccggtctggcctggccgtgccgcgaccactaccggcggtgatc
gctgacgccgcggcccgcaccgagccaccggaacccccgggcgcttacagcgccgctcgc
ggccggttcaatgacgacatcaccacgcagatcggcgggcaggttgcccggctatggaag
ctgacctcggcgttgaccatcgatgaccgcaccgggctgaccggcgtgcagtacaccgca
ccactacgcgaggacatgttgcgcgcgctgagccaatcgctaccacccgatacccgcaac
gggctggcccagcagcggctggccgtcgttggaaagacgatcgacgatcttttcggcgcg
gtgaccatcgtcaacccgggcggctcctacactctggccaccgagcacagtccgctgccg
ttggcgctgcataatggcctcgccgtgccaatccgggtccggctacaggtcgatgctccg
cccgggatgacggtggccgatgtcggtcagatcgagctaccgcccgggtacctgccgcta
cgagtaccaatcgaggtgaacttcacacagcgggttgccgtcgacgtgtcgctgcggacc
cccgacggcgtcgcgctgggtgaaccggtgcggttgtcggtgcactccaacgcctacggc
aaggtgttgttcgcgatcacgctatccgctgcggccgtgctggtaacgctggcgggccgg
cgcctttggcaccggttccgtggccagcctgatcgcgccgacctggatcgccccgacctg
cctaccggcaaacacgccccgcagcgccgtgccgtagccagtcgggatgacgaaaagcac
cgggta

COMPOSITIONS AND METHODS FOR DETECTING MULTIDRUG RESISTANT STRAINS OF *M. TUBERCULOSIS* HAVING MUTATIONS IN GENES OF THE MUTT FAMILY

This application claims the benefit of U.S. Provisional Patent Application No. 60/311,824, filed Aug. 14, 2001, and U.S. Provisional Patent Application No. 60/313,523, filed Aug. 21, 2001, the disclosures of each of which are incorporated herein by reference in their entirety.

BACKGROUND OF THE INVENTION

The present invention pertains to polynucleotides derived from *Mycobacterium tuberculosis* (*M. tuberculosis*) genes that aid in imparting resistance to antibiotics and chemically related compounds. This invention also relates to the use of the polynucleotides as oligonucleotide primers or probes for detecting *M. tuberculosis* strains that are resistant to antibiotics and related compounds in a biological sample. The present invention is also directed to diagnostic kits for detecting specific strains of *M. tuberculosis* expected to be contained in a biological sample.

Tuberculosis remains the world's leading infectious cause of adult deaths due to a single pathogen. Outbreaks of Multidrug-Resistant (MDR) tuberculosis defined as resistant to rifampicin and isoniazid are numerous, with low rates of treatment response and very high mortality. Some of these outbreaks involve patients with HIV infection (1, 2). In some reports, strains with a particular genotype have been identified, such as the "W" strain, which caused a major outbreak in New York (3).

In 1995, it was reported that the largest proportion of the *M. tuberculosis* strains from the Beijing area had highly similar IS6110 restriction fragment length polymorphism (RFLP) patterns and identical spoligo patterns (4). These strains were therefore designated "Beijing" genotype strains. The "W" variant strains in New York appeared to represent the Beijing genotype of *M. tuberculosis.* FIG. 1 depicts an example of the characteristic IS6110 RFLP and highly specific spoligo patterns of the Beijing genotype. The unexpected level of genetic conservation among *M. tuberculosis* isolates of the Beijing genotype led to the hypothesis that these strains may have selective advantages over other *M. tuberculosis* strains. Moreover, Beijing genotype strains were significantly associated with drug resistance in Cuba, Estonia, and Vietnam (vanSoolingen unpublished).

Several studies have suggested that strains of the Beijing genotype are emerging. In Vietnam, the proportion of Beijing strains was 71% in patients aged under 25, and 41% for those over 55 (vanSoolingen unpublished). Beijing strains have been implicated in several tuberculosis epidemics in the U.S.A. (3) and recently in Gran Canaria (5). A recent study showed that 82% of MDR strains isolated in a prison in Azerbaijan, Eastern Europe, are of the Beijing genotype (6).

Knowledge of a possible molecular basis for the acquisition of drug resistance in *M. tuberculosis* would be extremely useful as a prerequisite for appropriate treatment. Resistance to antibiotics in *M. tuberculosis* is due to genomic mutations in specific genes of the bacterium. In contrast to other Gram-positive or Gram-negative pathogens with MDR phenotypes, plasmid or transposon-mediated mechanisms of resistance have not been reported in *M. tuberculosis* (3,4,5).

Recent studies have provided evidence for a role of mutator phenotypes in the emergence of MDR clinical *Pseudomonas* isolates (6). Such phenotypes may enable the bacteria, not only to easily acquire resistance to several antibiotics, but also to adapt to new niches and to escape immune surveillance by modulating bacterial resistance to host defenses (7). This prompted an investigation into whether a similar situation might exist in *M. tuberculosis.* Since MDR strains are dangerous to manipulate, it was decided, as a first step, to simply look for the presence of mutations in genes expected to play a role in mutation frequency.

Mutator phenotypes commonly result from defects in DNA repair enzymes (8). An in silico analysis suggested that most mismatch repair systems, like mutS, mutL or mutH, are missing in the *M. tuberculosis* genome. However, the frequency of spontaneous mutations in *M. tuberculosis* (in vitro cultures) is similar to that found in other bacteria carrying mismatch repair systems. This characteristic could have significant implications with respect to genome stability and strain variability (9). This suggests that unknown sequences, similar to genes responsible for the repair of DNA lesions resulting from the alkylation or oxidation of nucleotides, are present in the genome of *M. tuberculosis.*

Thus, there was a need in the art to identify sequences in the genome of *M. tuberculosis* having similarity to genes responsible for the repair of DNA lesions responsible for alkylation or oxidation of nucleotides, such as the mut genes from *E. coli.* More particularly, there was a need to identify sequences similar to *E. coli* genes and other mut genes. There was a further need to develop methods of using these sequences to predict the epidemic character of a *Mycobacterium tuberculosis* isolate and/or a selective advantage to be maintained in the host and/or the acquisition of multiple drug resistance (MDR) by the isolate.

SUMMARY OF THE INVENTION

Accordingly, this invention aids in fulfilling these needs in the art. More particularly, this invention provides methods for predicting the epidemic character of a *Mycobacterium tuberculosis* isolate and/or a selective advantage to be maintained in the host and/or the acquisition of multiple drug resistance (MDR) by the isolate, wherein the method comprises detecting an alteration in the DNA repair system of the isolate. This invention provides specific pairs of oligonucleotide primers or probes that lead to fragments that hybridize specifically, under stringent hybridization conditions as defined hereinafter, to the nucleic acid (RNA or DNA) from a particular strain of *M. tuberculosis* that has the MDR phenotype. Methods and kits for detecting a strain of *M. tuberculosis* that has the MDR phenotype are also disclosed.

In a first aspect this invention involved an investigation of eleven multidrug resistant *M. tuberculosis* strains isolated in Spain in 1998, 1999, and 2000 (including five Beijing strains), one strain resistant to isoniazid and one strain sensitive to all antibiotics tested. Sensitivity to anti-tuberculosis drugs was assessed by the proportion method. Resistance to rifampicin was confirmed by demonstrating the presence of mutations in rpoB. In several cases, streptomycin resistance was confirmed by showing the presence of mutations in the rpsL or rrs gene. Mutations in putative mut genes were looked for by sequencing. The corresponding genetic regions were amplified and directly sequenced with the same primers. The study included data obtained form the published genome sequences of two isolates, H37Rv and CDC1551, which do not have a "Beijing" genotype.

The mutT2 sequence, the Rv3908 open reading frame (with a mutT domain), and rpoB, rpsL, and rrs sequences were first analyzed in eleven MDR strains (five strains with a "Beijing" genotype and six strains with a genotype other than "Beijing")and in three strains sensitive to all antibiotics tested (one strain with a Beijing genotype and two strains with a genotype other than Beijing). All MDR strains carried mutations in rpoB. All MDR strains with a Beijing genotype carried mutations in rpsL. All strains with a Beijing genotype (whether antibiotic sensitive or MDR) carried a mutation in Rv3908, a putative mutT gene. Three MDR strains with a Beijing genotype carried an additional mutation in mutT2.

It was discovered that *M. tuberculosis* strains of the "Beijing" genotype, which have been responsible for several outbreaks of MDR tuberculosis, carry a mutation in a putative mut gene. Three MDR strains with a "Beijing" genotype carry an additional mutation in a second putative mutT gene. These mutations may have provided these strains with a better adaptability to hostile environments, such that they constitute a higher risk for the patients to develop MDR tuberculosis, especially when these patients receive insufficient anti-tuberculosis treatments.

*M. tuberculosis* sequences similar to alkA and ogt sequence of *E. coli* were also investigated.

One strain out of six MDR strains with a genotype other than Beijing carry a mutation ACC→AGC at the $15^{th}$ annotated codon of ogt, leading to Thr→Ser.

Two MDR strains with Beijing genotype and one strain with a Beijing phenotype and sensitive to antibiotics carry a mutation of CGC→CTC at the $37^{th}$ annotated codon of ogt, leading to Arg→Leu.

Two MDR Beijing strains carry a silent change at the $12^{th}$ codon of ogt, GGG→GGA.

Four MDR Beijing strains carry a mutation ATC→GTC at the $12^{th}$ codon of alkA, leading to Ile→Val.

Accordingly, this invention provides a method for predicting the epidemic character of a *Mycobacterium tuberculosis* isolate and/or the acquisition of multiple drug resistance (MDR) by the isolate, wherein the method comprises detecting an alteration in the DNA repair system of the isolate. In one embodiment, the isolate contains a mutation in one or more mutT locus, and in particular a mutation at one or more mutT family member selected from the Rv3908 locus, the mutT2 locus, and the ogt locus. In another embodiment, the isolate consists essentially of a Beijing *Mycobacterium tuberculosis* strain. In further embodiments any of the above isolates can also contain a mutation in at least one locus selected from the group consisting of rpoB, rpsl, rrs, or rpsl.

To further investigate the correlation between mutations in mutT loci and the epidemic character of *M. tuberculosis* isolates, mut genes in 170 *M. tuberculosis* complex isolates from 38 different countries, including strains responsible for tuberculosis outbreaks were analyzed. The strains collected in a previous study performed under auspices of the European Concerted Action project on Molecular Epidemiology of Tuberculosis (4) were included in this collection. *M. tuberculosis* strains were previously grouped in 3 classes according to Sreevatsan et al. (14). The Beijing strains belong to class 1. Sixty four strains from class 1 including 34 Beijing strains, 47 strains of class 2, three strains of class 3, and 52 strains of an undetermined class were investigated. Eight Beijing strains were multidrug resistant (MDR). Sensitivity to anti-tuberculosis drugs was assessed by concentration methods. Resistance to rifampicin was confirmed by demonstrating the presence of mutations in the rpoB gene.

Mutations in putative mut genes were detected by DNA sequencing. Three mutT-homologous genes (mutT1, mutT2, and Rv3908), and ogt were examined in 169 strains. Data obtained from the published genome sequences of three isolates, strain MT210, which has a Beijing genotype, and strains H37Rv and CDC1551, which represent other genotypes, were also included.

The vast majority (31 out of 35 strains) of the Beijing strains analyzed carried a mutation replacing Arg 48 by Gly in the deduced polypeptide encoded by the mutT putative gene Rv3908. In addition, 23 out of these 31 strains carried another mutation replacing Gly 58 by Arg near the active site of the putative enzyme encoded by mutT2. Five of the eight Beijing strains carrying the mutation in Rv3908 but no mutation in mutT2, appeared to contain a mutation replacing Arg 37 by Leu in the deduced protein encoded by the putative ogt gene. Seven of the eight MDR Beijing strains analyzed contained the mutations in Rv3908 and mutT2 described above, whereas the eighth had mutations in Rv3908 and ogt. None of the 134 non-Beijing strains, representing a variety of genotypes contained mutations in these three genes. The Beijing strain, which was responsible for a recent epidemic in Gran Canaria (5) and which bore the mutations in Rv3908 and ogt, was shown to present an increased rate of mutation to rifampicin resistance.

This invention also provides a method for detecting a *Mycobacterium tuberculosis* strain having a multiple drug resistance (MDR) phenotype, wherein the method comprises detecting a mutation in the Rv3908 locus of the genome of the *Mycobacterium tuberculosis* strain. In one embodiment, the method comprises detecting a mutation at codon 48 of the Rv3908 locus, and in particular, the method comprises detecting GGG at codon 48.

Further, this invention provides a method for detecting a *Mycobacterium tuberculosis* strain having a multiple drug resistance (MDR) phenotype, wherein the method comprises detecting a mutation in the mutT2 locus of the genome of the *Mycobacterium tuberculosis* strain. In a further embodiment, the method comprises detecting a mutation at codon 58 of the mutT2 locus, in particular, detecting CGA at codon 58.

In another embodiment, this invention provides a method of detecting a *Mycobacterium tuberculosis* strain having a multiple drug resistance (MDR) phenotype, wherein the method comprises:

(a) providing a biological sample suspected of containing *Mycobacterium tuberculosis;*

(b) amplifying nucleic acids in the sample using as a primer pair (i) SEQ ID NO: 1, and SEQ ID NO: 2; or (ii) SEQ ID NO: 3, and SEQ ID NO: 4; or (iii) SEQ ID NO: 5, and SEQ ID NO: 6; or (iv) SEQ ID NO: 7, and SEQ ID NO: 8; and (c) detecting a mutation in the Rv3908 locus, or the mutT2 locus, or the ogt locus, or the alkA locus of the *Mycobacterium tuberculosis.*

In another embodiment, the isolate consists essentially of a Beijing *Mycobacterium tuberculosis* strain. In additional embodiments, the strain contains a mutation in one or more mutT family member selected from the Rv3908 locus, the mutT2 locus, and the ogt locus. In another embodiment, the isolate contains a mutation in at least one locus selected from the group consisting of rpoB, rpsl, rrs, or rpsl.

In another embodiment, the method comprises detecting a mutation in the Rv3908 locus of the genome of the *Mycobacterium tuberculosis* strain. In a further embodiment, the method comprises detecting a mutation at codon 48 of the Rv3908 locus. And in another embodiment, the method comprises detecting GGG at codon 48.

In another embodiment, the method comprises detecting a mutation in the mutT2 locus of the genome of the *Mycobacterium tuberculosis* strain. In a further embodiment, the method comprises detecting a mutation at codon 58 of the mutT2 locus. And in another embodiment, the method comprises detecting CGA at codon 58.

In another embodiment, the method comprises detecting a mutation in the ogt locus of the genome of the *Mycobacterium tuberculosis* strain.

This invention also provides a polynucleotide consisting of contiguous nucleotides of the Rv3908 locus of a *Mycobacterium tuberculosis* strain including codon 48 of said locus, or a polynucleotide fully complementary thereto. In one embodiment, codon 48 is GGG. In another embodiment, the polynucleotide contains the complement of SEQ ID NO: 1, SEQ ID NO: 2, or both SEQ ID NOs: 1 and 2.

Further, this invention provides a polynucleotide consisting of contiguous nucleotides of the mutT2 locus of a *Mycobacterium tuberculosis* strain including codon 58 of said locus, or a polynucleotide fully complementary thereto. In one embodiment, codon 48 is CGA. In another embodiment, the polynucleotide contains the complement of SEQ ID NO: 3, SEQ ID NO: 4, or both SEQ ID NOs: 3 and 4.

In addition, this invention provides a purified polynucleotide comprising a nucleotide sequence selected from:

a) SEQ ID NO: 1;
b) SEQ ID NO: 2;
c) SEQ ID NO: 3;
d) SEQ ID NO: 4;
e) SEQ ID NO: 5;
f) SEQ ID NO: 6;
g) SEQ ID NO: 7; and
h) SEQ ID NO: 8.

Additionally, the invention includes a purified polynucleotide that hybridizes specifically under stringent conditions with one or more polynucleotide sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

The invention further includes polynucleotide fragments capable of hybridization under stringent conditions with any one of the nucleotide sequences enumerated above.

Additionally, the invention includes kits for the detection of the presence of *M. tuberculosis* strains that contain the polynucleotide sequences set forth above.

In another embodiment, the invention provides:

- a polynucleotide fragment comprising SEQ ID NO: 1 (mutT2-1);
- a polynucleotide fragment comprising SEQ ID NO: 2 (mutT2-2);
- a polynucleotide fragment comprising SEQ ID NO: 3 (Rv3908-1);
- a polynucleotide fragment comprising SEQ ID NO: 4 (Rv3908-2);
- a polynucleotide fragment comprising SEQ ID NO: 5 (alkA-1);
- a polynucleotide fragment comprising SEQ ID NO: 6 (alkA-2);
- a polynucleotide fragment comprising SEQ ID NO: 7 (ogt-1); and
- a polynucleotide fragment comprising SEQ ID NO: 8 (ogt-2).

In another embodiment, the invention provides sequences of open reading frames of *M. tuberculosis* mut genes as follows:

- a purified polynucleotide of 1488 bp designated as alkA and consisting of SEQ ID NO: 27;
- a purified polynucleotide of 495 bp designated as ogt and consisting of SEQ ID NO: 28;
- a purified polynucleotide of 423 bp designated mutT2 and consisting of SEQ ID NO: 29;
- a purified polynucleotide of 744 bp designated Rv3908 and consisting of SEQ ID NO: 30;
- a purified polynucleotide of 912 bp designated mutY and consisting of SEQ ID NO: 31; and
- a purified polynucleotide of 2406 bp designated Rv3909 and consisting of SEQ ID NO: 32.

In another embodiment, the invention provides sequences of cDNA sequences of *M. tuberculosis* mut genes as follows:

- a purified polynucleotide comprising SEQ ID NO: 27 (alkA);
- a purified polynucleotide comprising SEQ ID NO: 28 (ogt);
- a purified polynucleotide comprising SEQ ID NO: 29 (mutT2);
- a purified polynucleotide comprising SEQ ID NO: 30 (Rv3908);
- a purified polynucleotide comprising SEQ ID NO: 31 (mutY); and
- a purified polynucleotide comprising SEQ ID NO: 32 (Rv3909).

In another embodiment, the invention provides purified polynucleotide sequences that are delimited upstream by the polynucleotide sequence of an upstream primer and downstream by the polynucleotide sequence of a downstream primer, wherein the purified polynucleotide sequence comprises the open reading frame sequence of a mut gene of the invention as follows:

- a purified polynucleotide sequence delimited upstream by the polynucleotide sequence of SEQ ID NO: 1 and downstream by the polynucleotide sequence of SEQ ID NO: 2, wherein the purified polynucleotide sequence comprises SEQ ID NO: 29;
- a purified polynucleotide sequence delimited upstream by the polynucleotide sequence of SEQ ID NO: 3 and downstream by the polynucleotide sequence of SEQ ID NO: 4, wherein the purified polynucleotide sequence comprises SEQ ID NO: 30;
- a purified polynucleotide sequence delimited upstream by the polynucleotide sequence of SEQ ID NO: 5 and downstream by the polynucleotide sequence of SEQ ID NO: 6, wherein the purified polynucleotide sequence comprises SEQ ID NO: 27; and
- a purified polynucleotide sequence delimited upstream by the polynucleotide sequence of SEQ ID NO: 7 and downstream by the polynucleotide sequence of SEQ ID NO: 8, wherein the purified polynucleotide sequence comprises SEQ ID NO: 28.

Still further, this invention provides a purified polynucleotide sequence originating from a gene of *M. tuberculosis* comprising a mutator allele.

In another embodiment, the invention provides:

- an *E. coli* strain containing the plasmid pMYC2501 deposited at the C.N.C.M. on Aug. 20, 2001 under Accession No. I-2711;
- an *E. coli* strain containing the plasmid pMYC2502 deposited at the C.N.C.M. on Aug. 20, 2001 under Accession No. I-2712; and
- an *E. coli* strain containing the plasmid pMYC2503 deposited at the C.N.C.M. on Aug. 20, 2001 under Accession No. I-2713.

Still further, this invention provides a method for detecting in a patient infected by *M. tuberculosis* a higher risk of being unable to eliminate the bacillus or a higher probability to develop MDR tuberculosis, wherein the method comprises detecting the presence of mutator alleles in clinical strains of *M. tuberculosis* with one or more polynucleotide fragments selected from SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

BRIEF DESCRIPTION OF THE DRAWINGS

This invention will be more fully described with reference to the figures, in which:

FIG. 1 depicts an example of the characteristic IS6110 RFLP and highly specific spoligo patterns of the Beijing genotype of *M. tuberculosis.*

FIGS. 2A-2C: FIGS. 2A and 2B show the sequence of the alkA locus, which is designated SEQ ID NO: 17. The sequences of primers alkA-1 (SEQ ID NO: 5) and alkA-2 (SEQ ID NO: 6) are indicated by underlining. FIG. 2C shows the sequence of the 1488 bp alkA open reading frame (ORF) (SEQ ID NO: 27).

FIGS. 3A-3B: FIG. 3A shows the sequence of the ogt locus, which is designated SEQ ID NO: 18. The sequences of primers ogt-1 (SEQ ID NO: 7) and ogt-2 (SEQ ID NO: 8) are indicated by underlining. Figure shows the sequence of the 495 bp ogt open reading frame (ORF) (SEQ ID NO: 28).

FIGS. 4A-4B: FIG. 4A shows the sequence of the mutT2 locus, which is designated SEQ ID NO: 19. The sequences of primers mutT2-1 (SEQ ID NO: 1) and mutT2-2 (SEQ ID NO: 2) are indicated by underlining. FIG. 4B shows the sequence of the 423 bp mutT2 open reading frame (ORF) (SEQ ID NO: 29).

FIGS. 5A-5B: FIG. 5A shows the sequence of the Rv3908 locus, which is designated SEQ ID NO: 20. The sequences of primers Rv3908-1-1 (SEQ ID NO: 3) and Rv3908-2 (SEQ ID NO: 3) are indicated by underlining. FIG. 5B shows the sequence of the 744 bp Rv3908 open reading frame (ORF) (SEQ ID NO: 30).

FIGS. 6A-6B: FIG. 6A shows the sequence of the mutY locus, which is designated SEQ ID NO: 21. The sequences of primers mutY-1 (SEQ ID NO: 9) and mutY-2 (SEQ ID NO: 10) are indicated by underlining. FIG. 6B shows the sequence of the 912 bp mutY open reading frame (ORF) (SEQ ID NO: 31).

FIGS. 7A-7C: FIGS. 7A and 7B show the sequence of the Rv3909 locus, which is designated SEQ ID NO: 22. FIG. 7C shows the sequence of the 2406 bp Rv3909 open reading frame (ORF) (SEQ ID NO: 32).

DETAILED DESCRIPTION OF THE INVENTION

*M. tuberculosis* strains with a "Beijing" genotype have been associated with outbreaks worldwide, including multidrug resistant (MDR) isolates like the "W" strain in the United States. An aim of this invention was to test the hypothesis of a better adaptation of "Beijing" *M. tuberculosis* due to alterations in DNA repair genes (mut genes). Similarly, other MDR strains (with a genotype other than Beijing) may accumulate mutations in DNA or nucleotide repair systems. Indeed, such alterations could result in increased frequencies of mutations in genes responsible for the resistance of the pathogen to different environments as well as to antibiotics, as described for *E. coli* and *Pseudomonas* species. In silico analysis of bacterial genomes provides a list of putative mut genes. mut and mutT putative genes in MDR *M. tuberculosis* isolates, including "Beijing" strains, were investigated as follows.

A network to monitor the spread of MDR-Tuberculosis in Spain based on genomic typing was set up in January 1998 by the Spanish Working Group on MDR-TB, coordinated by the Mycobacterial Genetic Unit of the University of Zaragoza and the Instituto de Salud Carlos III. All MDR strains defined as isolates with resistance to at least isoniazid (I) and rifampicin (R) isolated in 1998 in Spain were sent to the University of Zaragoza for molecular typing by the restriction fragment length polymorphism (RFLP) method using IS6110 (10). A total of 203 strains were registered. Among them 11 were of the Beijing family.

DNA samples of MDR strains were chosen with the criteria of, first exhibiting different restriction fragment length polymorphism (RFLP), and second containing enough DNA for an extensive analysis. In a first set of experiments five "Beijing" MDR strains and six MDR strains with a genotype other than "Beijing" were analyzed. One strain resistant to isoniazid and one strain susceptible to all antibiotics were analyzed, both having a genotype other than "Beijing".

Several putative mut genes were annotated as such in the released genome sequence of *M. tuberculosis.* In addition, using a BLAST, Rv3908 was identified as an ORF carrying a mutT domain (11, 12).

The following primers were designed to amplify putative mut genes:

```
mutT2:
mutT2-1:
5'-TCCGGATGATGATTTACCTCC-3',       SEQ ID NO:1

mutT2-2:
5'-TCCGCCGGGTCGGGGAC-3';           SEQ ID NO:2

Rv3908:
Rv3908-1:
5'-TCGAAGGTGGGCAAATCGTG-3',        SEQ ID NO:3

Rv3908-2:
5'-TGGGGTTCGCTGGAAGTGG-3';         SEQ ID NO:4

alkA:
alkA-1:
5'-AGCCGCGTAGGTAACCT-3',           SEQ ID NO:5

alkA-2:
5'-TGCTCGAGCATCCGCAG-3';           SEQ ID NO:6

ogt:
ogt-1:
5'-CAGCGCTCGCTGGCGCC-3',           SEQ ID NO:7

ogt-2:
5'-GACTCAGCCGCTCGCGA-3';           SEQ ID NO:8

mutY:
mutY-1:
5'-CCGGCGACGAATCGCTCGTT-3',        SEQ ID NO:9

mutY-2:
5'-AGCTGGGACAGTCGTCGCGG-3'.        SEQ ID NO:10

mutT1:
5'-ATCGTCGGCGTGCCGTG-3',           SEQ ID NO:23
5'-GTCAGCGTCCTGCCCGG-3'            SEQ ID NO:24

mutT3:
5'-GTCACGTCTGTTAGGACCTC-3',        SEQ ID NO:25
5'-CGCGCAACGGCTGCCGG-3'            SEQ ID NO:26
```

Similarly, primers were designed to amplify:

```
rpoB:
5'-TACGGTCGGCGAGCTGATCC-3'              SEQ ID NO:11

5'-TACGGCGTTTCGATGAACC-3';              SEQ ID NO:12

rrs:
5'-GAGAGTTTGATCCTGGCTCAG-3';            SEQ ID NO:13

5'-TGCACACAGGCCACAAGGGA-3'; and         SEQ ID NO:14

rpsl:
5'-GGCCGACAAACAGAACGT-3',               SEQ ID NO:15

5'-GTTCACCAACTGGGTGAC-3'.               SEQ ID NO:16
```

Amplification using primers mutT2-1 (SEQ ID NO: 1) and mutT2-2 (SEQ ID NO: 2) will result in a polynucleotide sequence delimited upstream by the polynucleotide sequence of SEQ ID NO: 1 and downstream by the polynucleotide sequence of SED ID NO: 2.

Amplification using primers Rv3908-1 (SEQ ID NO: 3) and Rv3908-2 (SEQ ID NO: 4) will result in a polynucleotide sequence delimited upstream by the polynucleotide sequence of SEQ ID NO: 3 and downstream by the polynucleotide sequence of SED ID NO: 4.

Amplification using primers alkA-1 (SEQ ID NO: 5) and alkA-2 (SEQ ID NO: 6) will result in a polynucleotide sequence delimited upstream by the polynucleotide sequence of SEQ ID NO: 5 and downstream by the polynucleotide sequence of SED ID NO: 6.

Amplification using primers ogt-1 (SEQ ID NO: 7) and ogt-2 (SEQ ID NO: 8) will result in a polynucleotide sequence delimited upstream by the polynucleotide sequence of SEQ ID NO: 7 and downstream by the polynucleotide sequence of SED ID NO: 8.

DNA sequencing was carried out directly on the amplified fragments by using the dideoxy chain-termination method with the Big Dye Terminator Cycle sequencing Kit (PE Applied Biosystems) on a GeneAmp PCR system 9600; Perkin Elmer) and run on a DNA analysis system model 373 (Applied Biosystems).

Sequences of mutY, mutT2, Rv3908, rpoB, mutT1, mutT3, ogt, rrs, and rpsl of strains H37Rv, CDC1551, and MT210 were obtained from published sequences (12) or at the TIGR WEB site. Several putative mut genes were annotated as such in the released genome sequence of *M. tuberculosis*. Using a BLAST, Rv3908 was identified as an ORF carrying a MutT domain (11, 12). Alleles of putative genes coding for DNA repair enzymes mutT (which hydrolyses 8-oxo-deoxyguanosine triphosphate) (13, 14) and mutY (specific adenine glycosylase) (8) were investigated in 11 MDR strains of *M. tuberculosis,* and 3 susceptible strains to all antibiotics plus one strain resistant to isoniazid that were taken as controls. In searches for sequences similar to mut T, mutT1, mutT2, mutT3, and RV3908 were discovered. The best fits were observed for mutT2 and Rv3908. The search for sequences similar to ogt and mutY identified a single open reading frame in each case.

The MDR and antibiotic sensitive strains were identified by classical identification tests. They were isolated from patients in Spain (the European collection of *M. tuberculosis* MDR strains). Five of the ten MDR strains and one sensitive strain had a "Beijing" genotype. Primers were designed to amplify the mutY, mutT2, Rv3908, rpoB, ogt, rrs, alkA, and rpsl gene candidates. For the mutY and mutM putative genes, amplification was obtained with all strains, but sequencing analysis did not reveal any mutation at these loci.

In all strains with a "Beijing" genotype, whether MDR or antibiotic sensitive, a mutation was discovered in Rv3908. Codon 48 (CGG) of the annotated ORF had been changed to GGG, which would lead to the substitution of Arg by Gly. No mutation in Rv3908 was observed in any other strain with a genotype other than "Beijing" (antibiotic sensitive or MDR).

Three out of four MDR "Beijing" strains had an additional mutation in mutT2, which led to a change in codon 58 (GGA to CGA) resulting in a substitution of Gly by Arg. The active site of the *E. coli* MutT enzyme comprises amino acids 53, 56, 57, and 98. Helix I of the polypeptide spans from aa 47 to 59 (15). Therefore, it would seem likely that a Gly→Arg mutation at position 58 would have a significant effect on enzyme activity and lead to a mutator phenotype, which in turn would facilitate the acquisition of genomic mutations resulting in resistance to antibiotics. Resistance to rifampicin was confirmed by showing mutations in rpoB for all MDR strains. An MDR *M. bovis* strain that was responsible for the B epidemic in Europe was investigated. This strain carries a mutation at the beginning of Rv3909, which seems to be arranged in an operon with RV3908. The different mutations are listed in Table 1.

TABLE 1 strain characteristics and analysis of mutations at rpoB, rpsI, rrs, Rv3908 and mut T2[#]

| Beijing MDR strains | Drugs susceptibility R/I/E/S | rpoB[a] | rpsI[b] | rrs[c] | Rv3908 | MutT2 | alkA | ogt |
|---|---|---|---|---|---|---|---|---|
| ZA 20 | R/I/S | Asp 516 Val | Lys 43 Arg | wt | Arg 48 Gly | wt | ND | Arg 37 Leu |
| ZA 65 | R/I/E/S | Asp 516 Val | Lys 43 Arg | wt | Arg 48 Gly | wt | Ile 12 Val | Arg 37 Leu |
| ZA 67 | R/I/E/S | His 526 Leu | Lys 43 Arg | wt | Arg 48 Gly | Gly 58 Arg | Ile 12 Val | ND |
| ZA 68 | R/I(at least) | Ser 531 Leu Val 577 Ala | Lys 43 Arg | wt | Arg 48 Gly | Gly 58 Arg | Ile 12 Val | ND |
| ZA 69 | R/I/S | Ser 531 Leu | Lys 43 Arg | wt | Arg 48 Gly | Gly 58 Arg | Ile 12 Val | ND |
| MDR strains other than Beijing | | | | | | | | |
| ZA 11 | R/I/E | Ser 531 Leu | wt | wt | wt | wt | wt | Thr 15 Ser |
| ZA 12 | R/I/E | ND | wt | wt | wt | wt | wt | wt |
| ZA 13 | R/I/S | His 526 Leu | Lys 43 Arg | wt | wt | wt | wt | wt |

TABLE 1-continued strain characteristics and analysis of mutations at rpoB, rpsI, rrs, Rv3908 and mut T2[#]

| Beijing MDR strains | Drugs susceptibility R/I/E/S | rpoB[a] | rpsI[b] | rrs[c] | Rv3908 | MutT2 | alkA | ogt |
|---|---|---|---|---|---|---|---|---|
| ZA 14 | R/I/E(at least) | His 526 Leu | wt | c491t | wt | wt | wt | wt |
| ZA 16 | R/I/E/S | Ser 531 Leu | wt | wt | wt | wt | wt | wt |
| ZA 17 | R/I/E/S | Asp 516 Val | wt | wt | wt | wt | ND | ND |
| Beijing strains | | | | | | | | |
| ZA 62 | sensitive | ND | ND | ND | Arg 48 Gly | wt | ND | Arg 37 Leu |
| Strains other than Beijing | | | | | | | | |
| *M. bovis* MDR ZA19 | R/I/E/S/ (at least) | Ser 531 Leu | Lys43Arg | wt | Rv3909 | wt | Ile 12 Val | wtt |
| ZA 15 | I/E | wt | wt | wt | wt | wt | wt | wt |
| CDC1551* | sensitive | wt | wt | wt | wt | wt | wt | wt |
| H37 Rv** | sensitive | wt | wt | wt | wt | wt | wt | wt |

*Analysis of the different loci using the sequences provided by TIGR: http://www.tigr.org
**Analysis of the different loci using the sequences provided by SANGER: http://www.sanger.ac.uk/
R = Rifampin I = Isoniazid E = Ethamutol S = Streptomycin
[a]Gene encoding the RNA polymerase subunit B
[b]Gene encoding ribosomal protein S12
[c]Gene encoding 16S rRNA
[#]For rpoB, rpsl, Rv3908, alkA, ogt, and mutT2: amino acid substitution; For rrs: nucleotide substitution. It is interesting to note in Table 1 that the three MDR "Beijing" strains with the same mutation at the putative mut T2 loci harbored a different rpoB mutation. The three strains were isolated from patients who had immigrated from Eastern Europe. These findings suggest that the two strains may correspond to the same outbreak. The acquisition of the three different mutations in rpoB leading to *rifampicin* resistance (5) must have occurred after the acquisition of mutations in the putative nucleotide repair enzyme genes Rv3908 and mutT2.

Resistance to streptomycin correlated with mutations at the rpsl locus for all MDR strains with a "Beijing" genotype. Strains with a genotype other than "Beijing" carried mutations at rrs (one strain), rpsl (one strain), or somewhere else and genetically unidentified (four strains) (4).

In a second set of experiments, mut genes in DNA of a total of 170 *M. tuberculosis* complex strains originating from 38 different countries were analyzed. This set comprised 149 *M. tuberculosis* strains, but also included other members of the complex, such as *M. bovis* (12), *M. bovis* BCG (3), *M. africanum* (2), *M. microti* (2), and *M. canettii* (1). Sixty-eight *M. tuberculosis* strains, including eight Beijing genotype strains, of which one was MDR, and the 20 strains of the other species mentioned above were selected, because they were characterized with 13 different genetic markers in previous studies (4, 21).

Furthermore, strains representing different branches of the Beijing genotype were included. Five *M. tuberculosis* strains of the Beijing genotype and one strain of another genotype were obtained from the national program for surveillance of MDR tuberculosis in Spain. Five *M. tuberculosis* Beijing genotype strains isolated in The Netherlands were included because they exhibited spoligo patterns with fewer than nine spacers. Five additional Beijing genotype strains were included. These strains exhibited hybridization to an additional spacer, as demonstrated using the extended set of spacers (vanSoolingen unpublished), two of which lacked hybridization to spacer. Four Beijing strains representing lineage's of the W-strain and originating in the U.S.A. were also included (22). Five Beijing isolates from patients living in Vietnam were selected because these strains acquired resistance in comparison with initial isolates of those patients. From ten patients, two follow-up isolates were included, of which the second showed an increase in drug resistance, four of these patients originated in Vietnam and six in The Netherlands, one was of the Beijing genotype. Fourteen additional non-Beijing strains were selected from The Netherlands, of which nine contained few IS6110 copies.

Finally, nineteen strains of another frequently observed genotype, the 'Haarlem genotype' (4) were investigated. Five of these originated from Bolivia, two were from an outbreak of MDR-TB in the Czech Republic (23), and twelve were of the "M-type" from Argentina (24).

To summarize, the collection consisted of 34 Beijing genotype isolates, 32 Haarlem genotype isolates, eight strains of the African genotype, four of the Hanoi type and 88 of other genotypes. For the majority of these strains the polymorphism in katG and gyrA, allowing the grouping according to Sreevatsan et al. 2, were known; 30 strains were of class 1, 47 of class 2, three of class 3 and 86 strains were of an undetermined class.

All isolates were subjected to at least IS6110 RFLP typing and Spoligotyping (4). Drug susceptibility testing according to the proportion method was done for 85 (51%) out of the 166 strains. Eighteen strains were resistant to solely INH, solely streptomycin, or to INH and streptomycin. Twenty strains from Argentina (n=9, all Haarlem), Spain (n=4, all Beijing), Vietnam (n=5, three Beijing, two other), China (n=1, Beijing) and The Netherlands (n=1, other) were MDR. All isolates were unique when the three typing methods were combined.

The sequences of the different genes mentioned above were determined in ten MDR *M. tuberculosis* strains including four Beijing strains. For the mutY, mutT1, and mutT3 putative genes, amplification was obtained with all strains tested, but sequence analysis did not reveal any mutation at these loci. However, in comparison with H37Rv and CDC1551, mutations in Rv3908, mutT2 and ogt were observed in MDR Beijing strains, but not in MDR strains with another genotype.

This investigation was extended to look for the presence of mutations in these three genes in the whole collection of *M. tuberculosis* complex isolates. The results are depicted in Tables 2 and 3.

TABLE 2

Distribution of mutations in the putative genes Rv3908, mutT2, and ogt among Beijing and non-Beijing genotype *M. tuberculosis* complex strains originating from 38 different countries.

| | Number of strains per affected locus | | | | |
|---|---|---|---|---|---|
| Genotype | Rv3908 | Rv3908 and mutT2 | Rv3908 and ogt | ogt | none |
| Beijing | 3[a] | 23[b] | 5[c] | 1[d] | 3[e] |
| Non-Beijing | 0 | 0 | 0 | 0 | 134[f] |

[A]*M. tuberculosis* strains from The Netherlands (2) and the USA (1).
[B]*M. tuberculosis* strains from China (1), Malaysia (2), Mongolia (1), The Netherlands (6), South Africa (2), Spain (3) Thailand (1), Vietnam (6); and the genome sequence of *M. tuberculosis* strain MT210 from TIGR.
[C]*M. tuberculosis* strains from The Netherlands (1), South Korea (1), Spain (2), and Vietnam (1).
[d]One *M. tuberculosis* strain from the USA.
[e]*M. tuberculosis* strains from The Netherlands (1) and the USA (2).
[f]114 *M. tuberculosis* strains from Argentina (14), Bolivia (7), Burundi (2), Canada (2), Central African Republic (2), Chile (2), China (1), Comoro Islands (1), Curacao (1), Czech Republic (4), Ethiopia (1), Ecuador (2), Greenland (2), Honduras (2), India (4), Italy (1), Iran (2), Mongolia (1), The Netherlands (33, including H37Ra), Russia (1), Rwanda (2), South Korea (1), Spain (3), Sri Lanka (2), Tahiti (2), Tanzania (2), Tunisia (2), Uganda (2), the USA (2), Vietnam (7), Zimbabwe (2), and CDC1551 from TIGR and H37Rv from SANGER; 12 *M. bovis* strains from Argentina (5), The Netherlands (6), and Saudi Arabia (1); three *M. bovis* BCG strains from Japan (1), The Netherlands (1), and Russia (1); two *M. africanum* strains from the Netherlands; two *M. microti* strains from the UK; and one *M. canettii* strain from Somalia.

TABLE 3

Affected loci in *M. tuberculosis* strains that are susceptible (S), resistant (DR) or multiresistant (MDR) to antibiotics.

| | | Affected locus | | | | |
|---|---|---|---|---|---|---|
| Genotype | Drug susceptibility | Rv3908 | Rv3908 and mutT2 | Rv3908 and Ogt | Ogt | None |
| Beijing | S | 2 | 12 | 2 | 0 | 1 |
| (n = 35) | DR | 0 | 3 | 1 | 0 | 0 |
| | MDR | 0 | 7 | 1 | 0 | 0 |
| | nd | 1 | 1 | 1 | 1 | 2 |
| Non-Beijing | S | 0 | 0 | 0 | 0 | 30 |
| (n = 134) | DR | 0 | 0 | 0 | 0 | 14 |
| | MDR | 0 | 0 | 0 | 0 | 12 |
| | nd | 0 | 0 | 0 | 0 | 78 |

Thirty-one out of 35 strains with a Beijing genotype, either susceptible to tuberculostatics or MDR, had a mutation in Rv3908. Codon 48 (CGG) of the annotated ORF had been changed to GGG, which would lead to the substitution of Arg by Gly (Table 2).

Five out of the 31 Beijing strains with the mutation in Rv3908 carried an additional mutation in ogt, implying a change in codon 37, resulting in a substitution of Arg by Leu. In addition, a single Beijing strain carried a mutation in ogt, but not in Rv3908 (Table 2).

Twenty-three out of 26 Beijing strains with the mutation in Rv3908, but lacking a mutation in ogt, had an additional mutation in mutT2, which leads to a change in codon 58 (GGA to CGA) resulting in a substitution of Gly by Arg.

It is noteworthy that all twelve of the MDR Beijing strains carried mutations in two mutT genes. Ten of the twelve carried mutations in Rv3908 and mutT2, and the remaining two had a mutation in both Rv3908 and ogt (see Table 3).

No mutations in Rv3908, mutT2, or ogt were observed in any of the 134 *M. tuberculosis* complex strains, originating from 38 different countries, with a genotype other than Beijing, including 30 strains of class 1. Thus, no mutations were observed in any of the 32 strains of the Haarlem genotype, including 14 DR and 12 MDR isolates, nor in any of the strains of *M. bovis, M. bovis* BCG, *M. africanum, M. microti,* and *M. canettii.*

The sequences of the three DNA repair genes (Rv3908, mutT2, and otg) were analyzed in 20 serial isolates of ten patients, in which the follow-up isolate showed an increase in resistance to anti-tuberculosis drugs. This analysis revealed that the sequences of the respective genes were unaltered, irrespective of the genotype. One of these patients was infected with a Beijing genotype strain, and the isolates of this patient had mutations in Rv3908 and mutT2. Four of the five additional follow-up isolates of the Beijing genotype that had gained resistance in comparison with previous isolates of the respective patients who suffered from a relapse of tuberculosis also showed mutations in Rv3908 and mutT, the fifth showed mutations in Rv3908 and ogt.

This invention provides the first demonstration of polymorphism in *M. tuberculosis* genes that might lead to a mutator phenotype, and therefore to a better adaptation of the bacilli to hostile environment (new ref. 28). The vast majority of Beijing strains carried the same mutation in ORF Rv3908, which contains a MutT domain. Seventy-four percent of the Beijing strains carried an additional and identical mutation in a second putative gene of the mutT family, whereas an additional 16% carried an additional and identical mutation in ogt. All eight MDR strains with a Beijing genotype were among strains carrying two mutations in putative mutator genes. This would support the notion that *M. tuberculosis* strains of the Beijing genotype may have adapted to hostile environments, including exposure to anti-tuberculosis drugs, due to a succession of alterations of DNA repair enzymes. Other genes involved in other DNA repair mechanism or in the fidelity of DNA replication may also be involved.

In less than 13% of the Beijing strains no mutation was observed in Rv3908. It is not clear whether these strains are ancestral to the mutator strains, or represent a separate lineage of the Beijing genotype strains. Two of the four Beijing strains devoid of a mutation in Rv3908 were in a separate branch of the dendrogram, when computer-assisted comparison of the IS6110 RFLP patterns using the unweighted pair group method for clustering was performed. Alternatively, the lack of a mutation in Rv3908 may be due to a reversion that could have occurred after a transient mutator phenotype. The presence of a mutation in mutT2 was always associated with a mutation in this ORF. This suggests that a first mutation occurred in Rv3908 and that thereafter a second mutation either in mutT2 or ogt was acquired. As observed for other bacterial populations, mutator phenotypes may be transient in many cases to limit deleterious effects (26).

It should be noted that, irrespective of the role that might be played by the mutations described herein, their presence provides a useful marker for predicting the epidemic character of a *Mycobacterium tuberculosis* isolate and/or a selective advantage to be maintained in the host and/or the acquisition of multiple drug resistance (MDR) by the isolate, wherein the method comprises detecting an alteration in the DNA repair system of said isolate.

This invention thus provides specific pairs of oligonucleotide primers or probes that lead to fragments that hybridize specifically, under stringent hybridization conditions as defined hereinafter, to the nucleic acid (RNA or DNA) from a particular strain of *M. tuberculosis* that has the MDR phenotype. These oligonucleotide primers include the following:

(A) SEQ ID NO: 1;
(B) SEQ ID NO: 2;
(C) SEQ ID NO: 3;
(D) SEQ ID NO: 4;
(E) SEQ ID NO: 5;
(F) SEQ ID NO: 6;
(G) SEQ ID NO: 7; and
(H) SEQ ID NO: 8.

In a specific embodiment of the present invention, the purified polynucleotides useful for detecting *M. tuberculosis* strains can be used in combination in order to detect MDR *M. tuberculosis* strains in a biological sample. Thus, the present invention also provides detection methods and kits comprising combinations of the purified polynucleotides according to the invention.

By "polynucleotides" according to the invention is meant the sequences referred to as SEQ ID NOs: 1, 2, 3, 4, 5, 6, 7, or 8 and the complementary sequences and/or the sequences of polynucleotides that hybridize to the referred sequences in specific stringent conditions and that are used for detecting *M. tuberculosis* strains carrying a gene that aids in imparting resistance to antibiotics, such as rifampicin and isoniazid or phenotypes that lead to resistances. The polynucleotides of SEQ ID NOs: 1-8 and their fragments can be used to select nucleotide primers notably for an amplification reaction, such as the amplification reactions further described.

PCR is described in U.S. Pat. No. 4,683,202 granted to Cetus Corp. The amplified fragments may be identified by agarose or polyacrylamide gel electrophoresis, or by a capillary electrophoresis, or alternatively by a chromatography technique (gel filtration, hydrophobic chromatography, or ion exchange chromatography). The specificity of the amplification can be ensured by a molecular hybridization using as nucleic probes the entire sequences or the polynucleotides of SEQ ID NOs: 1-8 and their fragments, oligonucleotides that are complementary to these polynucleotides or fragments thereof, or their amplification products themselves.

Amplified nucleotide fragments are useful as probes in hybridization reactions in order to detect the presence of one polynucleotide according to the present invention or in order to detect the presence of *M. tuberculosis* strains carrying genes that impart resistance to antibiotics. This invention also provides the amplified nucleic acid fragments ("amplicons") defined herein above. These probes and amplicons can be radioactively or non-radioactively labeled, using for example enzymes or fluorescent compounds.

Other techniques related to nucleic acid amplification can also be used and are generally preferred to the PCR technique. The Strand Displacement Amplification (SDA) technique is an isothermal amplification technique based on the ability of a restriction enzyme to cleave one of the strands at a recognition site (which is under a hemiphosphorothioate form), and on the property of a DNA polymerase to initiate the synthesis of a new strand from the 3' OH end generated by the restriction enzyme, and on the property of this DNA polymerase to displace the previously synthesized strand being localized downstream.

The SDA amplification technique is more easily performed than PCR (a single thermostated water bath device is necessary), and is faster than the other amplification methods. Thus, the present invention also comprises using the entire nucleic acid sequences or fragments thereof according to the invention (primers) in a method of DNA or RNA amplification according to the SDA technique.

The entire nucleotide sequences or polynucleotides of SEQ ID NOs: 1-8 and their fragments, especially the primers according to the invention, are useful as technical means for performing different target nucleic acid amplification methods such as:

TAS (Transcription-based Amplification System), described by Kwoh et al. (27);

SR (Self-Sustained Sequence Replication), described by Guatelli et al. (28);

NASBA (Nucleic acid Sequence Based Amplification), described by Kievitis et al., 1991 (29); and TMA (Transcription Mediated Amplification).

The polynucleotides of SEQ ID NOs: 1-8 and their fragments, especially the primers according to the invention, are also useful as technical means for performing methods for amplification or modification of a nucleic acid used as a probe, such as:

LCR (Ligase Chain Reaction), described by Landegren et al., 1988 (30), and improved by Barany et al. (31), who employ a thermostable ligase;

RCR (Repair Chain Reaction), described by Segev, D, et al. (32);

CPR (Cycling Probe Reaction), described by Duck et al. (33); and

Q-beta replicase reaction, described by Miele et al. in 1983 and improved by Chu et al. in 1986, Lizardi et al. in 1988, and by Burg et al. and Stone et al. in 1996.

When the target polynucleotide to be detected is RNA, for example mRNA, a reverse transcriptase enzyme can be used before the amplification reaction in order to obtain a cDNA from the RNA contained in the biological sample. The generated cDNA can be subsequently used as the nucleic acid target for the primers or the probes used in an amplification process or a detection process according to the present invention.

Nucleic acid probes according to the present invention are specific to produce an amplicon of the invention. By "specific probes" according to the invention is meant any oligonucleotide that hybridizes with one polynucleotide of SEQ ID NOs: 1-8 and which does not hybridize with unrelated sequences.

In a specific embodiment, the purified polynucleotides according to the present invention encompass polynucleotides having at least 75% homology in their entire nucleotide sequences or nucleic acid sequences with SEQ ID NOS: 1-8. By percentage of nucleotide homology according to the present invention is intended a percentage of identity between the corresponding bases of two homologous polynucleotides, this percentage of identity being purely statistical and the differences between two homologous polynucleotides being located at random and on the whole length of said polynucleotides.

The percent identity can be determined, for example, by comparing sequence information using the GAP computer program, version 6.0 described by Devereux et al. (34) and available from the University of Wisconsin Genetics Computer Group (UWGCG). The GAP program utilizes the alignment method of Needleman and Wunsch (35), as revised by Smith and Waterman (36). The preferred default parameters for the GAP program include: (1) a unary comparison matrix (containing a value of 1 for identities and 0 for non-identities) for nucleotides, and the weighted comparison matrix of Gribskov and Burgess (37) as described by Schwartz and Dayhoff, (38); (2) a penalty of 3.0 for each gap and an additional 0.10 penalty for each symbol in each gap; and (3) no penalty for end gaps.

The oligonucleotide probes according to the present invention hybridize under stringent conditions with *M. tuberculosis* DNA and RNA. As an illustrative embodiment, the stringent hybridization conditions used in order to specifically detect *M. tuberculosis* strains according to the present invention are advantageously the following:

Prehybridization and hybridization are performed at 68° C. in a mixture containing:

5×SSPE (1×SPE is 0.18 M NaCl, 10 mM $NaH_2PO_4$);
5×Denhardt's solution;
0.5% (w/v) sodium dodecyl sulfate (SDS); and
100 μg $ml^{-1}$ salmon sperm DNA.

The washings are performed as follows:

(a) Two washings at laboratory temperature for 10 min. in the presence of 2×SSPE and 0.1% SDS;
(b) One washing at 68° C. for 15 min. in the presence of 1×SSPE and 0.1% SDS; and
(c) One washing at 68° C. for 15 min. in the presence of 0.1×SSPE and 0.1% SDS.

The non-labeled polynucleotides or oligonucleotides of the invention can be directly used as probes. Nevertheless, the polynucleotides or oligonucleotides can be generally labeled with a radioactive element ($^{32}P$, 35S, $^3H$, 125I) or by a non-isotopic molecule (for example, biotin, acetylaminofluorene, digoxigenin, 5-bromodeoxyuridin, fluorescein) in order to generate probes that are useful for numerous applications. Examples of non-radioactive labeling of nucleic acid fragments are described in the French Patent No. FR 78 10975 or by Urdea et al. (39) or Sanchez-Pescador et al. (40).

Other labeling techniques can also be used, such as those described in the French patents 2 422 956 and 2 518 755. The hybridization step may be performed in different ways (Matthews et al. 1988). A general method comprises immobilizing the nucleic acid that has been extracted from the biological sample on a substrate (nitrocellulose, nylon, polystyrene) and then incubating, in defined conditions, the target nucleic acid with the probe. Subsequent to the hybridization step, the excess amount of the specific probe is discarded, and the hybrid molecules formed are detected by an appropriate method (radioactivity, fluorescence, or enzyme activity measurement).

In another advantageous embodiment of the present invention, the probes described herein can be used as "capture probes", and are for this purpose immobilized on a substrate in order to capture the target nucleic acid contained in a biological sample. The captured target nucleic acid is subsequently detected with a second probe, which recognizes a sequence of the target nucleic acid that is different from the sequence recognized by the capture probe.

The oligonucleotide fragments useful as probes or primers according to the present invention can be prepared by cleavage of the polynucleotides with restriction enzymes, as described in Sambrook et al. in 1989. Another appropriate preparation process of the nucleic acids of the invention containing at most 200 nucleotides (or 200 bp if these molecules are double-stranded) comprises the following steps:

Synthesizing DNA using the automated method of beta-cyanethylphosphoramidite described in 1986;
cloning the thus obtained nucleic acids in an appropriate vector; and
purifying the nucleic acid by hybridizing to an appropriate probe according to the present invention.

A chemical method for producing the nucleic acids according to the invention, which have a length of more than 200 nucleotides (or 200 bp if these molecules are double-stranded), comprises the following steps:

Assembling the chemically synthesized oligonucleotides having different restriction sites at each end;
cloning the thus obtained nucleic acids in an appropriate vector; and
purifying the nucleic acid by hybridizing to an appropriate probe according to the present invention.

The oligonucleotide probes according to the present invention can also be used in a detection device comprising a matrix library of probes immobilized on a substrate, the sequence of each probe of a given length being localized in a shift of one or several bases, one from the other, each probe of the matrix library thus being complementary to a distinct sequence of the target nucleic acid. Optionally, the substrate of the matrix can be a material able to act as an electron donor, the detection of the matrix positions in which hybridization has occurred being subsequently determined by an electronic device. Such matrix libraries of probes and methods of specific detection of a target nucleic acid are described in the European patent application No. 0 713 016, or PCT Application No. WO 95 33846, or also PCT Application No. WO 95 11995 (Affymax Technologies), PCT Application No. WO 97 02357 (Affymetrix Inc.), and also in U.S. Pat. No. 5,202,231 (Drmanac), said patents and patent applications being herein incorporated by reference.

The polynucleotide probes according to the invention can be incorporated into a kit for detecting the presence of *Mycobacterium tuberculosis*, wherein the kit comprises:

(A) a polynucleotide probe according to the invention; and
(B) reagents necessary to perform a nucleic acid hybridization reaction.

In one embodiment, the *Mycobacterium tuberculosis* is present in a biological sample, has resistance to antibiotics, and harbors one or more of the polynucleotide sequences according to the invention.

The primer pairs according to the invention can be incorporated into another kit for detecting the presence of *Mycobacterium tuberculosis*, wherein the kit comprises:

(A) a primer pair according to the invention; and
(B) reagents necessary to perform a nucleic acid amplification reaction.

In one embodiment, the *Mycobacterium tuberculosis* is present in a biological sample, has resistance to antibiotics, and harbors one or more of the polynucleotide sequences according to the invention.

In summary the results described above show that MDR strains of *M. tuberculosis* acquired mutations expected to result in a mutator phenotype. This invention provides the first evidence of polymorphism in putative genes of *M. tuberculosis* that correlate with a mutator phenotype, and therefore to a better adaptation of the *bacilli* to hostile environment (16). Results presented here show that all Beijing strains had a mutation in the ORF of Rv3908, which contains a MutT domain. Three of these Beijing strains, which also had an MDR phenotype, harbored an additional and identical mutation in a second putative gene of the mutT family. This suggests that *M. tuberculosis* strains adapt to hostile environments by a succession of alterations of DNA repair enzymes.

The acquisition of mutator alleles was described as an adaptive response of bacteria to a succession of different environments (17, 18). After infecting a host, *M. tuberculosis* has to adapt to different environments such as alveolar macrophages, then to granuloma containing unactivated macrophages, and then to activated macrophages after induction of the acquired immune responses. In addition, the bacilli have to adapt to the caseous media with low oxygen concentration in the center of tubercles, and then to different tissues during dissemination of the disease. Such variable growth conditions might select for mutator mutations in *M. tuberculosis* strains as described in other bacterial populations submitted to different environments. Mutations might occur with an increased frequency due to the toxic radicals produced in phagocytic cells. The accumulation of mutations leading to antibiotic resistance may be a consequence of the appearance of a mutator phenotype. MDR strains would be easily selected when patients with better adapted strains received inadequate anti-tuberculosis regimen.

An identification of the presence of mutator alleles in clinical strains allows one to identify the patients who present a higher risk of being unable to eliminate the *bacillus* or to develop MDR tuberculosis, and encourage clinicians to increased vigilance.

Plasmids containing polynucleotides of the invention have been deposited at the Collection Nationale de Cultures de Microorganismes ("C.N.C.M.") Institut Pasteur, 28, rue du Docteur Roux, 75724 Paris Cedex 15, France, as follows:

| Plasmid | Accession No. | Deposit Date |
|---|---|---|
| pMYC2501 | I-2711 | Aug. 20, 2001 |
| pMYC2502 | I-2712 | Aug. 20, 2001 |
| pMYC2503 | I-2713 | Aug. 20, 2001 |

A copy of the deposit receipt for each plasmid is attached hereto, and the entire contents of each deposit receipt are incorporated by reference herein.

REFERENCES

The following publications have been cited herein. The entire disclosure of each publication is relied upon and incorporated by reference herein.

1 Farmer P, Kim J Y. Community based approaches to the control of multidrug resistant tuberculosis: introducing "DOTS-plus". *BMJ* 1998; 317: 671-674.

2 Telzak E E, Sepkowitz K, Alpert P, Mannheimer S H, Medard F, El-Sadr W, Blum S, Gagliardi A, Salomon N, Turett G. Multi-Resistant Tuberculosis in patients without HIV infection. *NEJM* 1995; 333: 907-912.

3 Bifani P J. Identification of a W variant outbreak of *Mycobacterium tuberculosis* via population-based molecular epidemiology. *JAMA* 1999; 282(24): 2321-7.

4 Kremer K, van Soolingen D, Frothingham R, et al. Comparison of methods based on different molecular epidemiological markers for typing of *Mycobacterium tuberculosis* complex strains: interlaboratory study of discriminatory power and reproducibility. *Journal of Clinical Microbiology* 1999; 37(8): 2607-18.

5 Caminero J A. Epidemiological evidence of the spread of a *Mycobacterium tuberculosis* strain of the Beijing genotype on Gran Canaria Island. *American Journal of Respiratory & Critical Care Medicine* 2001; 164(7): 1165-70.

6 Pfyffer G E. Multidrug-resistant tuberculosis in prison inmates, Azerbaijan. *Emerging Infectious Diseases* 2001; 7(5): 855-61.

7 Van Rie A, Warren R, Mshanga I, Jordaan A M, Gian D, van der Spuy G D, Richardson M, Simpson J, Gie R P, Enarson D A, Beyers N, van Helden P D, Victor T C. Analysis for a limited number of gene codons can predict drug resistance of *Mycobacterium tuberculosis* in a high-incidence community. *J. Clin Microbiol* 2001; 39: 636-641.

8 Finken M, Kirschner P, Meier A, Wrede A, Bottger E C. Molecular basis of streptomycin resistance in *Mycobacterium tuberculosis*: alteraions of the ribosomal protein S12 gene and point mutations within a functional 16S ribosomal RNA pseudoknot. *Mol. Microbiol.* 1993; 9:1239-1246.

9 Telenti A, Imboden P, Marchesi F, Lowrie D, Cole S, Colston M J, Matter L, Schopfer K, Bodmer T. Detection of rifampicin-resistance mutations in *Mycobacterium tuberculosis*. *Lancet* 1993; 341: 647-650.

10 Oliver A, Canton R, Campo P, Baquero F, Blazquez J. High frequency of hypermutable *Pseudomonas aeruginosa* in Cystic Fibrosis Lun Infection. *Science* 2000; 288: 1251-1253.

11 Giraud A, Matic I, Tanillon O, Clara A, Radman M, Fons M, Taddei F. Costs and benefits of high mutation rates: Adaptive evolution of bacteria in the mouse gut. *Science* 2001; 291: 2606-2608.

12 Horst J P, Wu T H, Marinus M G. *Echerichia coli* mutator genes. *Trends Mirob* 1999; 7: 29-36.

13 Mizrahi V, Andersen S J. DNA repair in *Mycobacterium tuberculosis*. What have learnt from the genome sequence? *Mol Microbiol* 1998; 29: 1331-1339.

14 Sreevatsan S. Restricted structural gene polymorphism in the *Mycobacterium tuberculosis* complex indicates evolutionarily recent global dissemination. *PNAS USA* 1997; 94(18): 9869-74.

15 Samper S, Iglesias M J, Tello O. The Spanish multidrug resistant tuberculosis network. *Eurosurveillance* 2000; 5: 43-45.

16 Altschul S F, Madden T L, Schaffer, A A, Zhang J, Zhang Z, Miller W, Lipman D J. Gapped Blast and PSI Blast: a new generation of protein database search programs. *Nucleic Acid Res* 1997; 25: 3389-3402.

17 Cole S T, Brosch R, Parkhill J, Gamier T, Churcher C, Harris D, Gordon S V, Eiglmeier K, Gas S, Barry III C E, Tekaia F, Badcock K, Basham D, Brown D, Chillingworth T, Connor R, Davies R, Devlin K, Feltwell T, Gentles S, Hamlin N, Holroyd S, Homsby T, Jagles K, Kroghs A, Mclean J, Moule S, Morphy L, Oliver K, Osborne J, Quail M A, Rajandream M A, Rogers J, Rutter S, Seeger K, Skelton J, Squares R, Squares S, Sulston J E, Taylor K, Whitehead S, Barrell B G. Deciphering the biology of *Mycobacterium tuberculosis* from the complete genome sequence. *Nature* 1998; 393: 537-544.

18 Taddei F, Hayakawa H, Bouton M F, Cirinesi A M, Matic I, Sekiguchi M, Radman M. Counteraction by MutT protein of transcriptional errors caused by oxidative damage. *Science* 1997; 278: 128-130.

19 Cunningham R P. DNA repair: Caretakers of the genome? *Curr Biol* 1997; 7: 576-579.

20 Harris T K. Wu G, Massiah M A, Mildvan A S. Mutational, kinetic, and NMR studies of the roles of conserved glutamate residue and of Lysine-39 in the mechanism of the mutt pyrophosphohydrolase. *Biochemistry* 2000; 39: 1655-1674.
21 Supply P, Lesjean S, Savine E, Kremer K, van Soolingen D, Locht C. Automated high-throughput genotyping for study of global epidemiology of *Mycobacterium tuberculosis* based on mycobacterial interspersed repetitive units. *Journal of Clinical Microbiology* 2001; 39(10): 3563-71.
22 Kurepina N E, Sreevatsan S, Plikaytis B B, et al. Characterization of the phylogenetic distribution and chromosomal insertion sites of five IS6110 elements in *Mycobacterium tuberculosis*: non-random integration in the dnaA-dnaN region. *Tubercle & Lung Disease* 1998; 79(1): 31-42.
23 Kubin M, Havelkova M, Hyncicova I, et al. A multidrug-resistant tuberculosis microepidemic caused by genetically closely related *Mycobacterium tuberculosis* strains. *Journal of Clinical Microbiology* 1999; 37(8): 2715-6.
24 Ritacco V, Di Lonardo M, Reniero A, et al. Nosocomial spread of human immunodeficiency virus-related multidrug-resistant tuberculosis in Buenos Aires. *Journal of Infectious Diseases* 1997;176(3):637-42.
25 Tenaillon O. Mutators, population size, adaptive landscape and the adaptation of asexual populations of bacteria. *Genetics* 1999; 152(2): 485-93.
26 Taddei F. Role of mutator alleles in adaptive evolution. *Nature* 1997; 387(6634): 700-2.
27 Kwoh et al., *PNAS USA* 1989; 86:1173-77.
28 Guatelli et al., *PNAS USA* 1990; 87:1874-78.
29 Kievitis et al., *J. Virol. Methods* 1991; 35: 273-86.
30 Landegren et al., *Science* 1988; 241: 1077-80.
31 Barany et al. *PNAS USA;* 88:189-93.
32 Segev, D, et al., in "Non-radioactive Labeling and Detection of Biomolecules," Keasler, C., Springer Verlag, Berlin, N. Y., pp.197-205.
33 Duck et al., *Biotechnique* 1990; 9: 142-47.
34 Devereux et al., *Nucl. Acids Res.* 1984; 12: 387.
35 Needleman and Wunsch, *J. Mol. Biol.* 1970; 48:433.
36 Smith and Waterman, *Adv. Appl. Math* 1981; 2: 482.
37 Gribskov and Burgess, *Nucl. Acids Res.* 1986; 14: 6745.
38 Schwartz and Dayhoff, eds., Atlas of Protein Sequence and Structure, National Biomedical Search Foundation, pp. 353-358, 1979.
39 Urdea et al., *Nucleic Acids Research* 1988; 11: 4937-57.
40 Sanchez-Pescador et al., *J. Clin. Microbiol.* 1988; 26(10): 1934-38.
41 Tenaillon O, Toupance B, Nagard H L, Taddei F, Godelle B. Mutators, population size, adaptive landscape and adaptation of asexual populations of bacteria. *Genetics* 1999; 152: 485-493.
42 Rainey P B, Moxon E R. When being hyper keeps you fit. *Science* 2000; 288: 186-1187.
43 Taddei F, Radman M, Smith J M, Toupance B, Gouyon P H, Godelle B. Role of mutator alleles in adaptive evolution. *Nature* 1997; 387: 700-702.

---

What is claimed is:

1. A method of detecting a *Mycobacterium tuberculosis* strain having a Beijing genotype, wherein the method comprises:

(a) providing a biological sample suspected to contain *Mycobacterium tuberculosis* having an Beijing genotype; and (b) detecting an Arg 48 Gly mutation in the open reading frame of the *Mycobacterium tuberculosis* Rv3908 gene, as set forth in SEQ ID NO: 30, to thereby detect a *Mycobacterium tuberculosis* strain having a Beijing genotype.

2. The method of claim 1, further comprising amplifying nucleic acids in the sample using the primer pair SEQ ID NO: 3 and SEQ ID NO: 4.

3. The method of claim 1, wherein GGG is detected at codon 48.

4. The method of claim 2, wherein GGG is detected at codon 48.

5. The method of claim 1, wherein the method further comprises detecting a Gly 58 Arg mutation in the open reading frame of the *Mycobacterium tuberculosis* MutT2 gene, as set forth in SEQ ID NO: 29.

6. The method of claim 5, further comprising amplifying nucleic acids in the sample using the primer pair SEQ ID NO: 1 and SEQ ID NO: 2.

7. The method of claim 5, wherein CGA is detected at codon 58.

8. The method of claim 6, wherein CGA is detected at codon 58.

9. The method of claim 1, wherein the method further comprises detecting an Arg 37 Leu mutation in the open reading frame of the *Mycobacterium tuberculosis ogt* gene as set forth in SEQ ID NO: 28.

10. The method of claim 9, further comprising amplifying nucleic acids in the sample using the primer pair SEQ ID NO: 7 and SEQ ID NO: 8.

11. The method of claim 9, wherein CTC is detected at codon 37.

12. The method of claim 9, wherein CTC is detected at codon 37.

13. The method of claim 1, wherein the method further comprises detecting a silent GGG to GGA mutation in the twelfth codon of the open reading frame of the *Mycobacterium tuberculosis ogt* gene as set forth in SEQ ID NO: 28.

14. The method of claim 13, further comprising amplifying nucleic acids in the sample using the primer pair SEQ ID NO: 7 and SEQ ID NO: 8.

* * * * *

SEQUENCE LISTING

```
<160> NUMBER OF SEQ ID NOS: 32

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 1

tccggatgat gatttacctc c                                               21


<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 2

tccgccgggt cggggac                                                    17


<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3

tcgaaggtgg gcaaatcgtg                                                 20


<210> SEQ ID NO 4
<211> LENGTH: 19
```

-continued

```
<212> TYPE: DNA
<213> ORGANISM: Artificial Sequence
<220> FEATURE:
<223> OTHER INFORMATION: Description of Artificial Sequence: Primer

<400> SEQUENCE: 4

tggggttcgc tggaagtgg                                                   19


<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 5

agccgcgtag gtaacct                                                     17


<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 6

tgctcgagca tccgcag                                                     17


<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 7

cagcgctcgc tggcgcc                                                     17


<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 8

gactcagccg ctcgcga                                                     17


<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9

ccggcgacga atcgctcgtt                                                  20


<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
```

-continued agctgggaca gtcgtcgcgg 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
tacggtcggc gagctgatcc 20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 12
tacggcgttt cgatgaacc 19

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 13
gagagtttga tcctggctca g 21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
tgcacacagg ccacaaggga 20

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 15
ggccgacaaa cagaacgt 18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 16
gttcaccaac tgggtgac 18

<210> SEQ ID NO 17
<211> LENGTH: 2488
<212> TYPE: DNA
<213> ORGANISM: Mycobacterium tuberculosis -continued

<400> SEQUENCE: 17

```
ttggtcaaca agttcgaggg ggacgcgtcg ctaaccatct tcggcgcccc gaaccggctt     60
ccctgtcccg aagacaaggc actggccgcc gcgcgggcga tagccgatcg gctggtcaac    120
gaaatgcccg agtgccaggc cgggatcggc gtggcggcgg ggcaggtcat tgccggcaac    180
gtgggtgccc gagaacggtt cgagtacacc gtgatcgggg agccggtcaa cgaggcggcc    240
cgattgtgcg aactggccaa atcgcgtccc ggcaagttgc tggcttcggc acaggccgtg    300
gacgccgcaa gcgaagagga gcgcgcccgt tggtctttgg gtaggcatgt gaaacttcgt    360
gggcacgacc aaccggtccg gctggccaag ccggtcgggc tgaccaagcc gcgtaggtaa    420
cctgcccgaa cccacgacga ccccatcaca atgtcgtttt tccgccagtc atgtcggtgg    480
gcgggtgtaa ttgttgaagg gtgcacgacg acttcgaacg ctgctaccgg gcgatccagt    540
ccaaagacgc ccggttcgac ggctggttcg tcgtcgcggt tttgaccacc ggtgtctact    600
gccggccgag ttgccccgtc cggccaccgt tcgcgcgcaa tgtccggttc ctgccgactg    660
cggcggccgc tcagggggag ggattccggg cctgcaaacg gtgccgcccc gacgcctcgc    720
ctgggtctcc ggaatggaat gtgcgtagtg acgtcgtggc gcgggcgatg cggctgattg    780
ccgacggaac ggtggaccgc gacggtgtca gcggcctcgc ggcccagctc ggttacacca    840
ttcgccagct ggagcggctg ttgcaggccg tggtcggcgc cggtccgctc gcgttggccc    900
gcgcccaacg catgcagacc gcccgggtgc tgatcgagac cacgaacctg ccgttcggcg    960
atgtcgcatt cgccgccggg ttttccagca tccgtcagtt caacgacacc gttcgcctgg   1020
cgtgcgacgg cacaccgacg gcattgcgtg cgcgcgcggc cgcccgattc gagtctgcca   1080
ccgcatcagc gggcacggtg tcgctgcggc tacccgtccg tgcaccattc gccttcgagg   1140
gtgttttcgg ccatctggcc gccaccgcgg tgccgggttg cgaagaggtc cgcgatggtg   1200
cgtaccgacg cacgctacgg ctcccatggg gcaacggcat cgtcagcctg acgccggcac   1260
ccgatcatgt gcgctgcctg cttgtgctcg atgatttccg cgacctgatg acggccactg   1320
cacgttgccg acggctgctg gacctcgacg ccgatcccga agcgatcgtc gaggcgctgg   1380
gcgccgatcc ggatctgcgc gcagtggtgg gcaaggcacc cgggcaacgc attccccgca   1440
cagtcgacga ggcagaattc gccgtgcggg cggtcctcgc ccaacaggta tcgacgaagg   1500
ccgcaagcac tcacgcgggc cgactggtcg ccgcctacgg acggccggtc cacgatcgcc   1560
acggcgcttt gacccacacc ttcccgtcga tcgagcagct cgctgagatc gatcccggcc   1620
atctggccgt ccccaaggcg cgtcaaagga ccataaacgc gctcgtcgcc agccttgccg   1680
acaaaagtct ggtcctggac gccggatgtg actggcaacg cgcccgcggg cagttgctag   1740
cgctgcccgg agtgggcccc tggaccgcgg aggtcatcgc catgcgcggc ctcggtgacc   1800
cggacgcctt tccggccagt gatctcggcc tgcggctggc cgccaaaaag ctgggcctgc   1860
ctgcacaacg acgagccctg acggtgcaca gcgctcgctg gcgcccctgg cgctcctatg   1920
ccacccagca cctgtggacc accctggaac atccggtaaa ccaatggcca ccgcaggaga   1980
agatcgcatg attcactacc gcaccatcga tagccccatc gggccattaa ccctggccgg   2040
gcatggctcg gtgttgacga acctgcggat gctcgagcag acgtatgagc caagccgcac   2100
acactggaca cccgaccccg gcgcattttc tggcgctgtc gaccaactca acgcttattt   2160
cgccggcgag ctcaccgaat tcgatgtgga acttgacctc cggggaaccg actttcagca   2220
acgagtatgg aaagcattgc tgacaatccc gtacggggaa acccggtcct acggggaaat   2280
```

-continued

```
cgccgaccag atcggcgccc ccggcgccgc acgcgccgtg ggattggcca acggccacaa   2340

tcccatcgcc atcatcgtcc cgtgccaccg cgtgatcggc gccagcggaa agctcaccgg   2400

gtacggcggt ggaatcaacc ggaaacgagc tctgctcgag ttggagaaaa gccgggcgcc   2460

cgcagacttg acgctcttcg actgagcg                                      2488
```

<210> SEQ ID NO 18
<211> LENGTH: 895
<212> TYPE: DNA
<213> ORGANISM: Mycobacterium tuberculosis

<400> SEQUENCE: 18

```
ggcctcggtg acccggacgc ctttccggcc agtgatctcg gcctgcggct ggccgccaaa     60

aagctgggcc tgcctgcaca acgacgagcc ctgacggtgc acagcgctcg ctggcgcccc    120

tggcgctcct atgccaccca gcacctgtgg accaccctgg aacatccggt aaaccaatgg    180

ccaccgcagg agaagatcgc atgattcact accgcaccat cgatagcccc atcgggccat    240

taaccctggc cgggcatggc tcggtgttga cgaacctgcg gatgctcgag cagacgtatg    300

agccaagccg cacacactgg acacccgacc ccggcgcatt ttctggcgct gtcgaccaac    360

tcaacgctta tttcgccggc gagctcaccg aattcgatgt ggaacttgac ctccggggaa    420

ccgactttca gcaacgagta tggaaagcat tgctgacaat cccgtacggg gaaacccggt    480

cctacgggga aatcgccgac cagatcggcg cccccggcgc cgcacgcgcc gtgggattgg    540

ccaacggcca caatcccatc gccatcatcg tcccgtgcca ccgcgtgatc ggcgccagcg    600

gaaagctcac cgggtacggc ggtggaatca accggaaacg agctctgctc gagttggaga    660

aaagccgggc gcccgcagac ttgacgctct tcgactgagc gcccccgccc gcgagggtat    720

cgtcattgcg aaaatcgaag ccataattcg cccgctcgcg agcggctgag tcgatataaa    780

catacaaaaa caccaccgtt accgggggtg tttttgtatg ttcggcggtg tcctactttt    840

ccacccggag gggcagtatc atcggcgctg gcaggcttag cttccgggtt cggaa         895
```

<210> SEQ ID NO 19
<211> LENGTH: 823
<212> TYPE: DNA
<213> ORGANISM: Mycobacterium tuberculosis

<400> SEQUENCE: 19

```
gatgtccgga tgatgattta cctcctcggc tcgctcggcc acccggcgta cggcgtcgat     60

accggccata aacgtcggaa acttgattga cctacgcagg acaccaccgg cgcgctgcca    120

gccgttgagg tcgtgcagtg cggcgtcgac ctgctcatcc gttaacacag ccatacctcg    180

acggtatacc gtcacaggtc atgctgaatc agatcgtggt tgccggagcc atcgtccgcg    240

gttgcacggt cttggtggcg caacgcgttc ggccaccgga gttggcgggt cgttgggaac    300

ttcccggcgg taaggtcgcc gccggcgaaa ccgagcgcgc cgcgctggcc cgagagctcg    360

ccgaagaact gggactcgag gtcgccgacc tcgcggtggg cgaccgtgtg ggcgacgata    420

ttgcgttgaa cggcacgacg acgctgcggg cctatcgcgt gcatctgctt ggcggcgaac    480

cgcgtgcgcg tgaccaccgg gcgctgtgct gggtgacggc ggccgaactg cacgatgtcg    540

actgggtacc agccgaccgc ggctggattg cggacctggc gcgaaccctc aacgggtccg    600

ccgcagatgt ccaccgtcgc tgttaggaaa ccgacggtgt ggttgacggt ggccgccgtc    660

aacttggtta gaacaacgtg acaaaacgtt aacttgggtt tgcatgcccg tagcgattac    720

gatggttttc tggacgcgtg gcgacaactt ccgggcagga cgctgacgcc catccatcga    780
```

-continued gatacccgat gttgacgaga ggggtccccg acccggcgga ccg 823

<210> SEQ ID NO 20
<211> LENGTH: 1144
<212> TYPE: DNA
<213> ORGANISM: Mycobacterium tuberculosis

<400> SEQUENCE: 20
tgtcgctcga aggtgggcaa atcgtgcgcc cccgacacag cgacttctgt gatagatgtg 60
actggcgcga ctcaattggt cagcgcgggt cgcctgcacc gccccgctcc ctcgcccaac 120
gaataagtcc tggccgacga tgggcgctca gacggcgagt acatcgggaa cacccgcccg 180
taccagctac tatcgctggg gtgtccgacg gcgaacaagc caaatcacgt cgacgccggg 240
ggcggcgccg cgggcggcgc gctgcggcta cagccgagaa tcacatggac gcccaaccgg 300
ccggcgacgc caccccgacc ccggcaacgg cgaagcggtc ccggtcccgc tcacctcgtc 360
gcgggtcgac tcggatgcgc accgtgcacg aaacatcggc tggagggttg gtcattgacg 420
gtatcgacgg tccacgagac gcgcaggtcg cggctctgat cggccgcgtc gaccggcgcg 480
gccggctgct gtggtcgcta cccaaggggc acatcgagtt gggcgagacc gccgagcaga 540
ccgccatccg cgaggtcgcc gaggagaccg gcatccgcgg cagtgtgctc gccgcgctgg 600
ggcgcatcga ctactggttc gtcaccgacg gccggcgggt gcacaagacc gtccaccatt 660
atttgatgcg gtttttaggc ggagagctgt ccgacgaaga cctcgaggta gccgaggtag 720
cctgggtgcc gatccgggaa ctgccgtctc gactggccta cgccgacgaa cgtcgactag 780
ccgaggtggc cgacgaactg atcgacaagc tgcagagcga cggccccgcc gcgcttccgc 840
cgctaccacc cagctcgcct cgtcgacggc cgcaaacgca ttcacgcgct cgtcatgccg 900
atgactcagc accgggtcag cacaacggtc ccgggccggg gccgtgaccg cactgcaact 960
cggctgggcc gctttggcgc gcgtcacctc agcgatcggc gtcgtggccg gcctcgggat 1020
ggcgctcacg gtaccgtcgg cggcaccgca cgcgctcgca ggcgagccca gcccgacgcc 1080
ttttgtccag gtccgcatcg atcaggtgac cccggacgtg gtgaccactt ccagcgaacc 1140
ccat 1144

<210> SEQ ID NO 21
<211> LENGTH: 1312
<212> TYPE: DNA
<213> ORGANISM: Mycobacterium tuberculosis

<400> SEQUENCE: 21
cgcccaggcc ttggtcgaag atgatctcag cggccactcg gctgtccgcg cagccgaaga 60
tcaccgccgt gggcttctgc ccggcggcca agccggctcg gtggtcgacg ctctgactgg 120
gatgctgggg ccggccggcg acgaatcgct cgttaccctc tttgagtgct ttccacgcgg 180
ctaccggatt ggtgttgggc atgcctcaca tactgccgga accgtcggtg accggcccgc 240
gacacatatc agataccaat cttctcgctt ggtatcagcg atcgcaccgg gatctgccct 300
ggcgagagcc cggtgtcagc ccgtggcaga tcctggtcag cgagttcatg ctgcagcaga 360
cgccggccgc ccgggtgctg gcgatctggc cggactgggt gcggcggtgg cccacgccgt 420
cggccaccgc cacggccagc accgccgatg tgttacgcgc ctggggcaag ctgggctatc 480
ccaggcgagc caagcgctta cacgagtgcg ccaccgtcat cgcccgcgac cacaatgacg 540
tggtgcccga cgatatcgag atcctggtca ccctgccggg cgtcgggagc tacaccgcgc 600

-continued

```
gcgcggtggc gtgtttcgct taccgccagc gggtgccggt ggtggacacc aatgtgcggc     660
gcgtggtggc ccgcgccgtt cacggccgcg ccgacgccgg tgcgccatcg gtgccgcgcg     720
accacgccga cgtcttggcg ctgttgccgc accgcgagac ggcgcctgaa ttttcggtcg     780
cgctgatgga gttgggtgcg acggtgtgca ccgcccgcac accccggtgc gggttatgcc     840
cgctggactg gtgcgcatgg cggcatgccg gttatccgcc gtcggacggt ccgccgcgcc     900
gggggcaggc ctacaccgga accgaccgcc aagtccgcgg acggttactg gatgtgttgc     960
gcgccgcgga gtttcccgtc acccgggccg agttggacgt ggcgtggctg accgataccg    1020
cacagcgtga ccgggcgctg gagtcgctgc tggccgatgc gctggtgacc cggacggtcg    1080
atggccggtt cgcgttgccc ggcgaagggt tttagccggg taggccgtcc gcaccggcgg    1140
cgccgaaacc gccgggatca ccggggttgc ccgcgacgac tgtcccagct cccgcggcgc    1200
cacccgcgcc gccagcgccg ccggcacctc cctggccccc ggtaccgccc gcaccgtgga    1260
cacctggctg gctgaacatt ccggcacctc cgccggcacc tccggcaccg cc            1312
```

<210> SEQ ID NO 22
<211> LENGTH: 2806
<212> TYPE: DNA
<213> ORGANISM: Mycobacterium tuberculosis

<400> SEQUENCE: 22

```
ccgtctcgac tggcctacgc cgacgaacgt cgactagccg aggtggccga cgaactgatc      60
gacaagctgc agagcgacgg ccccgccgcg cttccgccgc taccacccag ctcgcctcgt     120
cgacggccgc aaacgcattc acgcgctcgt catgccgatg actcagcacc gggtcagcac     180
aacggtcccg ggccggggcc gtgaccgcac tgcaactcgg ctgggccgct ttggcgcgcg     240
tcacctcagc gatcggcgtc gtggccggcc tcgggatggc gctcacggta ccgtcggcgg     300
caccgcacgc gctcgcaggc gagcccagcc cgacgccttt tgtccaggtc cgcatcgatc     360
aggtgacccc ggacgtggtg accacttcca gcgaacccca tgtcaccgtc agcggaacgg     420
tgaccaatac cggtgaccgc ccagtccgcg atgtgatggt ccggcttgag cacgccgccg     480
cggtcacgtc gtcaacggcg ttacgcacct cgctcgacgg cggcaccgac cagtaccagc     540
cggccgcgga cttcctcacg gtcgcccccg aactagaccg cgggcaagag gccggcttta     600
ccctctcggc cccgctgcgc tcgctgacca ggccgtcgtt ggccgtcaac cagcccggga     660
tctacccggt cctggtcaac gtcaatggga cacccgacta cggtgcgcct gcgcggctcg     720
acaatgcgcg gttcctgttg cccgtggtcg gagtgccacc cgaccaggcc accgacttcg     780
gctccgctgt tgcaccagaa acgacggcgc cggtctggat caccatgctg tggccgctgg     840
ccgaccggcc ccggttggcc cccggggcac ccggtggcac cgttcccgtc cggctggtcg     900
acgacgacct ggcaaactcg ctggccaacg gcggccggct ggacatcctc ctgtcggcgg     960
ccgagttcgc caccaaccgg gaagtcgacc ccgacggcgc cgtcggccga gcgctgtgcc    1020
tggccatcga cccagatcta ctcatcaccg tcaatgcgat gaccggcggc tacgtcgtgt    1080
ccgactcgcc cgacggggcc gctcaactac cgggcacccc gacccacccg ggcaccggcc    1140
aggccgccgc atccagctgg ctggatcgat tgcggacgct agtccaccgg acatgcgtga    1200
cgccgctgcc ttttgcccaa gccgacctgg atgctttgca gcgggttaat gatccgaggc    1260
tgagcgcgat cgcaaccatc agccccgccg acatcgtcga ccgcatcctg gatgtcagct    1320
ccacccgcgg cgcaaccgtg ctgcccgacg gcccgttgac cggccgggcg atcaacttgc    1380
tcagcaccca cggcaacacg gttgccgtcg cggccgccga ttttagcccc gaggaacagc    1440
```

-continued agggttcgtc ccagatcggc tccgcgctct tacccgctac cgcgccccgg cggttgtccc 1500
cgcgggtggt agcggcgccg tttgatcccg cggtcggggc cgcgctggcc gccgcgggaa 1560
caaacccgac cgttcctacc tatctagatc cctcgttgtt cgttcggatc gcgcatgaat 1620
cgatcaccgc gcgccgccag gacgccttgg gcgcaatgct gtggcgcagc ttggagccga 1680
atgccgcgcc ccgtacccaa atcctggtgc cgcccggcgtc gtggagcctg gccagcgacg 1740
acgcgcaggt catcctgacc gcgctggcca ccgccatccg gtctggcctg gccgtgccgc 1800
gaccactacc ggcggtgatc gctgacgccg cggcccgcac cgagccaccg gaaccccccgg 1860 gcgcttacag cgccgctcgc ggccggttca atgacgacat caccacgcag atcggcgggc 1920
aggttgcccg gctatggaag ctgacctcgg cgttgaccat cgatgaccgc accgggctga 1980
ccggcgtgca gtacaccgca ccactacgcg aggacatgtt gcgcgcgctg agccaatcgc 2040
taccacccga tacccgcaac gggctggccc agcagcggct ggccgtcgtt ggaaagacga 2100
tcgacgatct tttcggcgcg gtgaccatcg tcaacccggg cggctcctac actctggcca 2160
ccgagcacag tccgctgccg ttggcgctgc ataatggcct cgccgtgcca atccgggtcc 2220
ggctacaggt cgatgctccg cccgggatga cggtggccga tgtcggtcag atcgagctac 2280
cgcccgggta cctgccgcta cgagtaccaa tcgaggtgaa cttcacacag cgggttgccg 2340
tcgacgtgtc gctgcggacc cccgacggcg tcgcgctggg tgaaccggtg cggttgtcgg 2400
tgcactccaa cgcctacggc aaggtgttgt tcgcgatcac gctatccgct gcggccgtgc 2460
tggtaacgct ggcgggccgg cgcctttggc accggttccg tggccagcct gatcgcgccg 2520
acctggatcg ccccgacctg cctaccggca aacacgcccc gcagcgccgt gccgtagcca 2580
gtcgggatga cgaaaagcac cgggtatgag accctcccct ggagaggtgc ccacggcatc 2640
gcagaggcag cccgagctgt ccgacgcggc gctggtatcg cactcctggg caatggcatt 2700
cgcgacgctg atcagccgga tcaccggctt tgcccggatc gtgctgctgg ccgcgatctt 2760
aggtgcggcg ctggccagct cgttctcggt ggccaaccag ctgccg 2806

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 23
atcgtcggcg tgccgtg 17

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 24
gtcagcgtcc tgcccgg 17

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Primer -continued

<400> SEQUENCE: 25
gtcacgtctg ttaggacctc 20

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 26
cgcgcaacgg ctgccgg 17

<210> SEQ ID NO 27
<211> LENGTH: 1458
<212> TYPE: DNA
<213> ORGANISM: Mycobacterium tuberculosis

<400> SEQUENCE: 27
gtgcacgacg acttcgaacg ctgctaccgg gcgatccagt ccaaagacgc ccggttcgac 60
ggctggttcg tcgtcgcggt tttgaccacc ggtgtctact gccggccgag ttgccccgtc 120
cggccaccgt tcgcgcgcaa tgtccggttc ctgccgactg cggcggccgc tcagggggag 180
ggattccggg cctgcaaacg gtgccgcccc gacgcctcgc ctgggtctcc ggaatggaat 240
gtgcgtagtg acgtcgtggc gcgggcgatg cggctgattg ccgacggaac ggtggaccgc 300
gacggtgtca gcggcctcgc ggcccagctc ggttacacca ttcgccagct ggagcggctg 360
ttgcaggccg tggtcggcgc cggtccgctc gcgttggccc gcgcccaacg catgcagacc 420
gcccgggtgc tgatcgagac cacgaacctg ccgttcggcg atgtcgcatt cgccgccggg 480
ttttccagca tccgtcagtt caacgacacc gttcgcctgg cgtgcgacgg cacaccgacg 540
gcattgcgtg cgcgcgcggc cgcccgattc gagtctgcca ccgcatcagc gggcacggtg 600
tcgctgcggc tacccgtccg tgcaccattc gccttcgagg gtgttttcgg ccatctggcc 660
gccaccgcgg tgccgggttg cgaagaggtc cgcgatggtg cgtaccgacg cacgctacgg 720
ctcccatggg gcaacggcat cgtcagcctg acgccggcac ccgatcatgt gcgctgcctg 780
cttgtgctcg atgatttccg cgacctgatg acggccactg cacgttgccg acggctgctg 840
gacctcgacg ccgatcccga agcgatcgtc gaggcgctgg gcgccgatcc ggatctgcgc 900
gcagtggtgg gcaaggcacc cggcaacgc attccccgca cagtcgacga ggcagaattc 960
gccgtgcggg cggtcctcgc ccaacaggta tcgacgaagg ccgcaagcac tcacgcgggc 1020
cgactggtcg ccgcctacgg acggccggtc cacgatcgcc acggcgcttt gacccacacc 1080
ttcccgtcga tcgagcagct cgctgagatc gatcccggcc atctggccgt ccccaaggcg 1140
cgtcaaagga ccataaacgc gctcgtcgcc gccggatgtg actggcaacg cgcccgcggg 1200
cagttgctag cgctgcccgg agtgggcccc tggaccgcgg aggtcatcgc catgcgcggc 1260
ctcggtgacc cggacgcctt tccggccagt gatctcggcc tgcggctggc cgccaaaaag 1320
ctgggcctgc ctgcacaacg acgagccctg acggtgcaca gcgctcgctg gcgcccctgg 1380
cgctcctatg ccacccagca cctgtggacc accctggaac atccggtaaa ccaatggcca 1440
ccgcaggaga agatcgca 1458

<210> SEQ ID NO 28
<211> LENGTH: 495
<212> TYPE: DNA
<213> ORGANISM: Mycobacterium tuberculosis -continued

<400> SEQUENCE: 28

```
atgattcact accgcaccat cgatagcccc atcgggccat taaccctggc cgggcatggc     60

tcggtgttga cgaacctgcg gatgctcgag cagacgtatg agccaagccg cacacactgg    120

acacccgacc ccggcgcatt ttctggcgct gtcgaccaac tcaacgctta tttcgccggc    180

gagctcaccg aattcgatgt ggaacttgac ctccggggaa ccgactttca gcaacgagta    240

tggaaagcat tgctgacaat cccgtacggg gaaacccggt cctacgggga aatcgccgac    300

cagatcggcg cccccggcgc cgcacgcgcc gtgggattgg ccaacggcca caatcccatc    360

gccatcatcg tcccgtgcca ccgcgtgatc ggcgccagcg gaaagctcac cgggtacggc    420

ggtggaatca accggaaacg agctctgctc gagttggaga aaagccgggc gcccgcagac    480

ttgacgctct tcgac                                                     495
```

<210> SEQ ID NO 29
<211> LENGTH: 423
<212> TYPE: DNA
<213> ORGANISM: Mycobacterium tuberculosis

<400> SEQUENCE: 29

```
atgctgaatc agatcgtggt tgccggagcc atcgtccgcg gttgcacggt cttggtggcg     60

caacgcgttc ggccaccgga gttggcgggt cgttgggaac ttcccggcgg taaggtcgcc    120

gccggcgaaa ccgagcgcgc cgcgctggcc cgagagctcg ccgaagaact gggactcgag    180

gtcgccgacc tcgcggtggg cgaccgtgtg ggcgacgata ttgcgttgaa cggcacgacg    240

acgctgcggg cctatcgcgt gcatctgctt ggcggcgaac cgcgtgcgcg tgaccaccgg    300

gcgctgtgct gggtgacggc ggccgaactg cacgatgtcg actgggtacc agccgaccgc    360

ggctggattg cggacctggc gcgaaccctc aacgggtccg ccgcagatgt ccaccgtcgc    420

tgt                                                                  423
```

<210> SEQ ID NO 30
<211> LENGTH: 744
<212> TYPE: DNA
<213> ORGANISM: Mycobacterium tuberculosis

<400> SEQUENCE: 30

```
gtgtccgacg gcgaacaagc caaatcacgt cgacgccggg ggcggcgccg cgggcggcgc     60

gctgcggcta cagccgagaa tcacatggac gcccaaccgg ccggcgacgc caccccgacc    120

ccggcaacgg cgaagcggtc ccggtcccgc tcacctcgtc gcgggtcgac tcggatgcgc    180

accgtgcacg aaacatcggc tggagggttg gtcattgacg gtatcgacgg tccacgagac    240

gcgcaggtcg cggctctgat cggccgcgtc gaccggcgcg gccggctgct gtggtcgcta    300

cccaaggggc acatcgagtt gggcgagacc gccgagcaga ccgccatccg cgaggtcgcc    360

gaggagaccg gcatccgcgg cagtgtgctc gccgcgctgg ggcgcatcga ctactggttc    420

gtcaccgacg gccggcgggt gcacaagacc gtccaccatt atttgatgcg gtttttaggc    480

ggagagctgt ccgacgaaga cctcgaggta gccgaggtag cctgggtgcc gatccgggaa    540

ctgccgtctc gactggccta cgccgacgaa cgtcgactag ccgaggtggc cgacgaactg    600

atcgacaagc tgcagagcga cggccccgcc gcgcttccgc cgctaccacc cagctcgcct    660

cgtcgacggc cgcaaacgca ttcacgcgct cgtcatgccg atgactcagc accgggtcag    720

cacaacggtc ccgggccggg gccg                                           744
```

-continued

<210> SEQ ID NO 31
<211> LENGTH: 912
<212> TYPE: DNA
<213> ORGANISM: Mycobacterium tuberculosis

<400> SEQUENCE: 31
atgcctcaca tactgccgga accgtcggtg accggcccgc gacacatatc agataccaat 60
cttctcgctt ggtatcagcg atcgcaccgg gatctgccct ggcgagagcc cggtgtcagc 120
ccgtggcaga tcctggtcag cgagttcatg ctgcagcaga cgccggccgc ccgggtgctg 180
gcgatctggc cggactgggt gcggcggtgg cccacgccgt cggccaccgc cacggccagc 240
accgccgatg tgttacgcgc ctggggcaag ctgggctatc ccaggcgagc caagcgctta 300
cacgagtgcg ccaccgtcat cgcccgcgac cacaatgacg tggtgcccga cgatatcgag 360
atcctggtca ccctgccggg cgtcgggagc tacaccgcgc gcgcggtggc gtgtttcgct 420
taccgccagc gggtgccggt ggtggacacc aatgtgcggc gcgtggtggc ccgcgccgtt 480
cacggccgcg ccgacgccgg tgcgccatcg gtgccgcgcg accacgccga cgtcttggcg 540
ctgttgccgc accgcgagac ggcgcctgaa ttttcggtcg cgctgatgga gttgggtgcg 600
acggtgtgca ccgcccgcac accccggtgc gggttatgcc cgctggactg gtgcgcatgg 660
cggcatgccg gttatccgcc gtcggacggt ccgccgcgcc gggggcaggc ctacaccgga 720
accgaccgcc aagtccgcgg acggttactg gatgtgttgc gcgccgcgga gtttcccgtc 780
acccgggccg agttggacgt ggcgtggctg accgataccg cacagcgtga ccgggcgctg 840
gagtcgctgc tggccgatgc gctggtgacc cggacggtcg atggccggtt cgcgttgccc 900
ggcgaagggt tt 912

<210> SEQ ID NO 32
<211> LENGTH: 2406
<212> TYPE: DNA
<213> ORGANISM: Mycobacterium tuberculosis

<400> SEQUENCE: 32
gtgaccgcac tgcaactcgg ctgggccgct ttggcgcgcg tcacctcagc gatcggcgtc 60
gtggccggcc tcgggatggc gctcacggta ccgtcggcgg caccgcacgc gctcgcaggc 120
gagcccagcc cgacgccttt tgtccaggtc cgcatcgatc aggtgacccc ggacgtggtg 180
accacttcca gcgaacccca tgtcaccgtc agcggaacgg tgaccaatac cggtgaccgc 240
ccagtccgcg atgtgatggt ccggcttgag cacgccgccg cggtcacgtc gtcaacggcg 300
ttacgcacct cgctcgacgg cggcaccgac cagtaccagc cggccgcgga cttcctcacg 360
gtcgcccccg aactagaccg cgggcaagag gccggcttta ccctctcggc cccgctgcgc 420
tcgctgacca ggccgtcgtt ggccgtcaac cagcccggga tctacccggt cctggtcaac 480
gtcaatggga cacccgacta cggtgcgcct gcgcggctcg acaatgcgcg gttcctgttg 540
cccgtggtcg gagtgccacc cgaccaggcc accgacttcg gctccgctgt tgcaccagaa 600
acgacggcgc cggtctggat caccatgctg tggccgctgg ccgaccggcc ccggttggcc 660
cccggggcac ccggtggcac cgttcccgtc cggctggtcg acgacgacct ggcaaactcg 720
ctggccaacg gcggccggct ggacatcctc ctgtcggcgg ccgagttcgc caccaaccgg 780
gaagtcgacc ccgacggcgc cgtcggccga gcgctgtgcc tggccatcga cccagatcta 840
ctcatcaccg tcaatgcgat gaccggcggc tacgtcgtgt ccgactcgcc cgacggggcc 900
gctcaactac cgggcacccc gacccacccg ggcaccggcc aggccgccgc atccagctgg 960

-continued

```
ctggatcgat tgcggacgct agtccaccgg acatgcgtga cgccgctgcc ttttgcccaa   1020
gccgacctgg atgctttgca gcgggttaat gatccgaggc tgagcgcgat cgcaaccatc   1080
agccccgccg acatcgtcga ccgcatcctg gatgtcagct ccacccgcgg cgcaaccgtg   1140
ctgcccgacg gcccgttgac cggccgggcg atcaacttgc tcagcaccca cggcaacacg   1200
gttgccgtcg cggccgccga ttttagcccc gaggaacagc agggttcgtc ccagatcggc   1260
tccgcgctct tacccgctac cgcgccccgg cggttgtccc cgcgggtggt agcggcgccg   1320
tttgatcccg cggtcggggc cgcgctggcc gccgcgggaa caaacccgac cgttcctacc   1380
tatctagatc cctcgttgtt cgttcggatc gcgcatgaat cgatcaccgc gcgccgccag   1440
gacgccttgg gcgcaatgct gtggcgcagc ttggagccga atgccgcgcc ccgtacccaa   1500
atcctggtgc cgccggcgtc gtggagcctg gccagcgacg acgcgcaggt catcctgacc   1560
gcgctggcca ccgccatccg gtctggcctg gccgtgccgc gaccactacc ggcggtgatc   1620
gctgacgccg cggcccgcac cgagccaccg gaacccccgg gcgcttacag cgccgctcgc   1680
ggccggttca atgacgacat caccacgcag atcggcgggc aggttgcccg gctatggaag   1740
ctgacctcgg cgttgaccat cgatgaccgc accgggctga ccggcgtgca gtacaccgca   1800
ccactacgcg aggacatgtt gcgcgcgctg agccaatcgc taccacccga tacccgcaac   1860
gggctggccc agcagcggct ggccgtcgtt ggaaagacga tcgacgatct tttcggcgcg   1920
gtgaccatcg tcaacccggg cggctcctac actctggcca ccgagcacag tccgctgccg   1980
ttggcgctgc ataatggcct cgccgtgcca atccgggtcc ggctacaggt cgatgctccg   2040
cccgggatga cggtggccga tgtcggtcag atcgagctac cgcccgggta cctgccgcta   2100
cgagtaccaa tcgaggtgaa cttcacacag cgggttgccg tcgacgtgtc gctgcggacc   2160
cccgacggcg tcgcgctggg tgaaccggtg cggttgtcgg tgcactccaa cgcctacggc   2220
aaggtgttgt tcgcgatcac gctatccgct gcggccgtgc tggtaacgct ggcgggccgg   2280
cgcctttggc accggttccg tggccagcct gatcgcgccg acctggatcg ccccgacctg   2340
cctaccggca aacacgcccc gcagcgccgt gccgtagcca gtcgggatga cgaaaagcac   2400
cgggta                                                              2406
```